(12) United States Patent
Stern et al.

(10) Patent No.: US 7,740,889 B2
(45) Date of Patent: Jun. 22, 2010

(54) BACTERIOCINS AND NOVEL BACTERIAL STRAINS

(75) Inventors: Norman J Stern, Athens, GA (US); Edward A Svetoch, Serpukhov District (RU); Boris V Eruslanov, Serpukhov District (RU); Vladimir V Perelygin, Serpukhov District (RU); Vladimir P Levchuk, Serpukhov District (RU); Nikolay N Urakov, Olympic vill. (RU); Larisa I Volodina, Serpukhov District (RU); Yuri N. Kovalev, Serpukhov District (RU); Tamara Y. Kudryavtseva, Serpukhov District (RU); Victor D. Pokhilenko, Serpukhov District (RU); Valery N. Borzenkov, Serpukhov District (RU); Olga E. Svetoch, Serpukhov District (RU); Eugeni V. Mitsevich, Serpukhov District (RU); Irina P. Mitsevich, Serpukhov District (RU)

(73) Assignees: The United States of America as represented by the Secretary of Agriculture, Washington, DC (US); State Research Center for Applied Microbiology & Biotechnology, Ministry of Health & Social Development, RF, as represented by Director of the State Research Center for Applied Microbiology & Biotechnology, Ministry of Health & Social Development, RF, Obolensk (RU)

(*) Notice: Subject to any disclaimer, the term of this patent is extended or adjusted under 35 U.S.C. 154(b) by 146 days.

(21) Appl. No.: 11/859,166

(22) Filed: Sep. 21, 2007

(65) Prior Publication Data

US 2009/0068722 A1  Mar. 12, 2009

Related U.S. Application Data

(62) Division of application No. 11/129,337, filed on May 13, 2005, now Pat. No. 7,321,024.

(51) Int. Cl.
A23B 7/10 (2006.01)
(52) U.S. Cl. .................... 426/53; 424/234.1; 435/69.1; 530/350
(58) Field of Classification Search .................. None
See application file for complete search history.

(56) References Cited

U.S. PATENT DOCUMENTS

| 4,980,163 A | 12/1990 | Blackburn et al. |
|---|---|---|
| 5,302,388 A | 4/1994 | Doyle et al. |
| 5,945,333 A | 8/1999 | Rehberger |
| 6,255,080 B1 | 7/2001 | Teather et al. |
| 6,403,082 B1 | 6/2002 | Stiles et al. |
| 6,448,224 B1 | 9/2002 | Novak et al. |
| 6,451,365 B1 | 9/2002 | King et al. |
| 6,461,607 B1 | 10/2002 | Farmer |
| 6,503,881 B2 | 1/2003 | Krieger et al. |
| 6,515,016 B2 | 2/2003 | Hunter |

OTHER PUBLICATIONS

U.S. Patent Application Publication No. US 2002/0176910 A1, Raczek, Nov. 28, 2002.
Cherif, A., et al., "Thuricin 7: A Novel Bacteriocin Produced by *Bacillus thuringiensis* BMG1.7, a New Strain Isolated From Soil", *Letters in Applied Microbiology*, vol. 32, pp. 243-247, 2001.
Ennahar, S., et al., "Clas IIa Bacteriocins : Biosynthesis, Structure and Activity", *FEMS Micr. Reviews*, vol. 24, pp. 85-106, 2000.
Jack, R., et al., "Bacteriocins of Gram-Positive Bacteria", *Microbiological Reviews*, vol. 59,(2), pp. 171-200, Jun. 1995.
Martirani, L., et al., "Purification and Partial Characterization of Bacillocin 490, a Novel Bacteriocin Produced by a Thermophilic Strain of *Bacillus licheniformis*", *Microbial Cell Factories*, vol. 1,(1), pp. 1-5, 2002.
Piuri, M., et al., "A Novel Antimicrobial Activity of a *Paenibacillus Polymyxa* Strain Isolated From Regional Fermented Sausages", *Letters in Applied Microbiology*, vol. 27, pp. 9-13, 1998.

*Primary Examiner*—Jennifer E Graser
(74) *Attorney, Agent, or Firm*—John D. Fada; Gail E. Poulos

(57) ABSTRACT

Novel bacteriocins produced by novel bacterial strains are used for at least reducing the levels of colonization by at least one target bacteria in animals, especially poultry.

4 Claims, 4 Drawing Sheets

| | |
|---|---|
| Bacillocin 602    N | ATYYGNGLYCNKQKHYTWVDWNKASREIGKIIVNGWVQH |
| Bacillocin 1580   N | VNYGNGVSCSKTKCSVNWGHTHQAFRVTSGVASG |
| Bacillocin B37 | FVYGNGVTSILVQAQFLVNG QRRFFYTPDK |
| Lactococcin MMFII | TSYGNGVHCNKSKCWIDVSELETYKAGTVSNPKDILW |
| Mesentericin Y105 | KYYGNGVHCTKSGCSVNWGEAASAGIHRLANGGNGFW |
| Leucocin A | KYYGNGVHCTKSGCSVNWGEAFSAGVHRLANGGNGFW |
| Bifidocin B | KYYGNGVTCGLHDCRVDRGKATCGIINNGGMWGDIG |
| Sakacin P | KYYGNGVHCGKHSCTVDWGTAIGNIGNNAAANWATGGNAGWNK |
| Mundticin | KYYGNGVSCNKKGCSVDWGKAIGIIGNNSAANLATGGAAGWSK |
| Sakacin A | ARSYGNGVYCNKKCWVNRGEATQSIIGGMISGWASGLAGM |
| Pisciolin-126 | KYYGNGVSCNKNGCTVDWSKAIGIIGNNAAANLTTGGAAGWNKG |
| Carnobacteriocin BM1 | AISYGNGVYCNKEKCWVNKAENKQAITGIVIGGWASSLAGMGH |
| Carnobacteriocin B2 | VNYGNGVSCSKTKCSVNWGQAFQERYTAGINSFVSGVASGAGSIGRRP |
| Bavaricin MN | TKYYGNGVYCNSKKCWVDWGQAAGGIGQTVVXGWLGGAIPGK |
| Bacteriocin 31 | ATYYGNGLYCNKQKCWVDWNKASREIGKIIVNGWVQHGPWAPR |
| Enterocin P | ATRSYGNGVYCNNSKCWVNWGEAKENIAGIVISGWASGLAGMGH |
| Enterocin A | THHSGKYYGNGVYCTKNKCTVDWAKATTCIAGMSIGGFLGGAIPGKC |
| Pediocin PA-1 | KYYGNGVTCGKHSCSVDWGKATTCIINNGAMAXATGGHQGNHKX |
| Divercin V41 | TKYYGNGVYCNSKKCWVDWGQASGCIGQTVVGGWLGGAIPGKC |
| CoaA | KYYGNGVTCGKHSCSVDWGKATTCIINNGAMAWATGGHQGTHKC |
| Consensua | YGNGV C   C V  W   A |

Fig. 4

BACTERIOCINS AND NOVEL BACTERIAL STRAINS

This is a divisional of application Ser. No. 11/129,337, filed May 13, 2005, now U.S. Pat. No. 7,321,024 issued Jan. 22, 2008, which is herein incorporated by reference in its entirety.

BACKGROUND OF THE INVENTION

1. Field of the Invention

This invention relates to the control of disease in animals, especially poultry, through the use of novel bacteriocin-producing *Paenibacillus* and *Bacillus* species and/or novel bacteriocins produced by these species. It also relates to novel bacteriocins, amino acid sequences of the novel bacteriocins, and to the strains of *Paenibacillus* or *Bacillus* producing the novel bacteriocins. Furthermore, the invention relates to therapeutic compositions containing the novel bacteriocins and/or the strains of *Paenibacillus* or *Bacillus* producing them and to uses of the therapeutic compositions.

2. Description of the Related Art

The consumption of improperly prepared poultry products has resulted in human intestinal diseases. It has long been recognized that *Salmonella* spp. are causative agents of such diseases and more recently, *Campylobacter* spp., especially *Campylobacter jejuni*, has also been implicated. Both microorganisms may colonize poultry gastrointestinal tracts without any deleterious effects on the birds, and although some colonized birds can be detected, asymptomatic carriers can freely spread the microorganisms during production and processing, resulting in further contamination of both live birds and carcasses. Poultry serves as the primary reservoir for *Salmonella* and *Campylobacter* in the food supply (Jones et al., Journal of Food Protection, Volume 54, No. 7, 502-507, July, 1991). Prevention of colonization in live poultry during growout production may diminish the problem of poultry contamination.

A number of factors contribute to the colonization and continued presence of bacteria within the digestive tract of animals. These factors have been extensively reviewed by Savage (Progress in Food and Nutrition Science, Volume 7, 65-74, 1983). Included among these factors are: (1) Gastric acidity (Gilliland, Journal of Food Production, Volume 42, 164-167, 1979); (2) bile salts (Sharpe & Mattick, Milchwissenschaft, Volume 12, 348-349, 1967; Floch et al., American Journal of Clinical Nutrition, Volume 25, 1418-1426, 1972; Lewis & Gorbach, Archives of Internal Medicine, Volume 130, 545-549, 1972; Gilliland and Speck, Journal of Food Protection, Volume 40, 820-823, 1977); Hugdahl et al., Infection and Immunity, Volume 56, 1560-1566, 1988); (3) peristalsis; (4) digestive enzymes (Marmur, Journal of Molecular Biology, Volume 3, 208-218, 1961); (5) immune response; and (6) indigenous microorganisms and the antibacterial compounds which they produce. The first four factors are dependent on the phenotype of the host and may not be practically controllable variables. The immune response in the gastrointestinal (GI) tract is not easily modulated. The factors involving indigenous microorganisms and their metabolites are dependent on the normal flora of the GI tract.

One potential approach to control *Campylobacter* and/or *Salmonella* colonization is through the use of competitive exclusion (CE) Nurmi and Rantala (Nature, Volume 241, 210-211, 1973) demonstrated effective control of *Salmonella* infection by gavaging bacteria from healthy poultry intestinal materials into young chicks whose microflora had not yet been established, against *Salmonella* colonization. Administration of undefined CE preparations to chicks speeds the maturation of gut flora in newly-hatched birds and provides a substitute for the natural process of transmission of microflora from the adult hen to its offspring. Results from laboratory and field investigations provide evidence of benefits in *Campylobacter* control through administering normal microflora to chickens; decreased frequency of *Campylobacter*-infected flocks (Mulder and Bolder, IN: Colonization Control of human bacterial enteropathogens in poultry; L. C. Blankenship (ed.), Academic Press, San Diego, Calif., 359-363, 1991) and reduced levels of *Campylobacter jejuni* (*C. jejuni*) in the feces of colonized birds has been reported (Stern, Poultry Science, Volume 73, 402-407, 1994).

Schoeni and Wong (Appl. Environ. Microbiol., Volume 60, 1191-1197, 1994) reported a significant reduction in broiler colonization by *C. jejuni* through the application of carbohydrate supplements together with three identified antagonists: *Citrobacter diversus* 22, *Klebsiella pneumoniae* 23, and *Escherichia coli* 25. There is also evidence of a significant decrease of *C. jejuni* in intestinal samples from infected broilers after treatment with poultry-isolated cultures of *Lactobacillus acidophilus* and *Streptococcus faecium* (Morishita et al. Avian Diseases, Volume 41, 850-855, 1997).

Snoeyenbos et al. (U.S. Pat. No. 4,335,107, June, 1982) developed a competitive exclusion (CE) microflora technique for preventing *Salmonella* colonization by lyophilizing fecal droppings and culturing this preparation anaerobically. Mikola et al. (U.S. Pat. No. 4,657,762, April, 1987) used intestinal fecal and cecal contents as a source of CE microflora for preventing *Salmonella* colonization. Stern et al. (U.S. Pat. No. 5,451,400, September, 1995 and U.S. Pat. No. 6,241,335, April 2001) disclose a mucosal CE composition for protection of poultry and livestock against colonizations by *Salmonella* and *Campylobacter* where the mucin layer of prewashed caeca is scraped and the scrapings, kept in an oxygen-free environment, are cultured anaerobically. Nisbet et al. (U.S. Pat. No. 5,478,557, December, 1996) disclose a defined probiotic that can be obtained from a variety of domestic animals which is obtained by continuous culture of a batch culture produced directly from fecal droppings, cecal and/or large intestine contents of the adult target animal.

Microorganisms produce a variety of compounds which demonstrate anti-bacterial properties. One group of these compounds, the bacteriocins, consists of bactericidal proteins with a mechanism of action similar to ionophore antibiotics. Bacteriocins are often active against species which are closely related to the producer. Their widespread occurrence in bacterial species isolated from complex microbial communities such as the intestinal tract, the oral or other epithelial surfaces, suggests that bacteriocins may have a regulatory role in terms of population dynamics within bacterial ecosystems. Bacteriocins are defined as compounds produced by bacteria that have a biologically active protein moiety and bactericidal action (Tagg et al., Bacteriological Reviews, Volume 40, 722-256, 1976). Other characteristics may include: (1) a narrow inhibitory spectrum of activity centered about closely related species; (2) attachment to specific cell receptors; and (3) plasmid-borne genetic determinants of bacteriocin production and of host cell bacteriocin immunity. Incompletely defined antagonistic substances have been termed "bacteriocin-like substances". Some bacteriocins effective against Gram-positive bacteria, in contrast to Gram-negative bacteria, have wider spectrum of activity. It has been suggested that the term bacteriocin, when used to describe inhibitory agents produced by Gram-positive bacteria, should meet the minimum criteria of (1) being a peptide and (2) possessing bactericidal activity (Tagg et al., supra).

Diverse biological activities are common among *Bacillus* spp. This genus can produce pronounced antagonism to pathogenic microorganisms. To create this antagonism, bacilli may manifest amylolytic, cellulolytic, lipolytic, proteolytic, and pectinolytic activities. They can generate lysozyme and are effectively involved in synthesis of numerous amino acids and other biologically active substances (Zani et al., Journal of Applied Microbiology, Volume 84, 68-71, 1988; Sorokulova et al., Anitbiotiki i Khemioterpaiya, Volume 41 (10), 13-15, 1992). Except for *Bacillus anthracis* and *B. cereus*, members of the genus *Bacillus* are harmless for warm-blooded host animals and have phylogenetic relatedness to lactobacilli (Fox, Science, Volume 209, No. 4455, page 457, 1980). Owing to these desirable characteristics, bacteria within the genus *Bacillus* spp. have found wide application as probiotics and are widely used in medicine and veterinary practice (Smirnov et al, Microbiol. J., Volume 54(6), 82-93, 1992).

Raczek (United States Patent Application US2002/0176910, published Nov. 28, 2002) discloses the use of a composition that contains live or dead microorganisms which secrete bacteriocins, or the bacteriocins themselves or in combinations thereof, for use with feedstuffs for agricultural livestock.

Puiri et al. (Letters in Applied Microbiology, Volume 27, 9-13, 1998) disclose a novel antimicrobial compound secreted by a *Paenibacillus polymyxa* strain isolated from fermented sausages. The bacteriocin-like properties included a proteinaceous nature (sensitive to proteases), insensitivity to organic solvents and chelators, stability to heat (up to 10 minutes at 90° C.), and acidic pH but instability in alkaline conditions. The bacteriocin-like compound has a molecular mass of 10 kDa. It showed inhibitory activity to several species of *Bacillus, Paenibacillus, Lactobacillus, Micrococcus luteus, Escherichia coli, Klebsiella pneumoniae, Proteus vulgaris*, and *Serratia marcescens*. It showed no inhibitory activity to *Staphylococcus aureus, Pseudomonas aeruginosa*, or *Salmonella newport*.

The present invention provides novel compositions containing a novel strain of a *Paenibacillus* or *Bacillus* species and/or novel bacteriocins produced by the novel strains; a method of using the strain or bacteriocin, the novel strains, amino acid sequences for the novel bacteriocins, and methods of use, all of which are different from related art strains, bacteriocins, and methods of using.

SUMMARY OF THE INVENTION

It is therefore an object of the present invention to provide novel strains of *Bacillus* and *Paenibacillus* that produce novel bacteriocins.

A further object of the present invention is to provide a novel *Paenibacillus polymyxa* having the identifying characteristics of NRRL B-30507.

A still further object of the present invention is to provide a novel *Paenibacillus polymyxa* having the identifying characteristics of NRRL B-30508.

Another object of the present invention is to provide a novel *Paenibacillus polymyxa* having the identifying characteristics of NRRL B-30509.

A still further object of the present invention is to provide a novel *Bacillus circulans* having the identifying characteristics of NRRL B-30644.

A further object of the present invention is to provide novel bacteriocins produced by a novel strains of *Bacillus* and *Paenibacillus*.

A still further object of the present invention is to provide a novel bacteriocin having an amino acid sequence as set forth in SEQ ID NO 1.

A still further object of the present invention is to provide a novel bacteriocin having an amino acid sequence as set forth in SEQ ID NO 2.

A still further object of the present invention is to provide a novel, bacteriocin having an amino acid sequence as set forth in SEQ ID NO 3.

Another object of the present invention is to provide a method for at least reducing the levels of colonization by at least one target bacteria in animals by administering to the animal a therapeutic composition including at least one novel strain of *Bacillus* or *Paenibacillus* that produces a novel bacteriocin, at least one novel bacteriocin produced by a novel strain of *Bacillus* or *Paenibacillus*, or a combination of the novel strains and novel bacteriocins.

A further object of the present invention is to provide a method for at least reducing levels of colonization by at least one target bacteria in animals by administering to the animal a therapeutic composition including a novel strain of *Paenibacillus polymyxa* having the characteristics of NRRL Deposit No. B-30507, B30508, B-30509, B-30644, and mixtures thereof.

A still further object of the present invention is to provide a method for at least reducing the levels of colonization by at least one target bacteria in animals by administering to the animal a therapeutic composition including a novel bacteriocin having an amino acid sequence as set forth in SEQ ID NO 1.

A still further object of the present invention is to provide a method for at least reducing the levels of colonization by at least on target bacteria in animals by administering to the animal a therapeutic composition including a novel bacteriocin having an amino acid sequence as set forth in SEQ ID NO 2.

A still further object of the present invention is to provide a method for at least reducing the levels of colonization by at least on target bacteria in animals by administering to the animal a therapeutic composition including a novel bacteriocin having an amino acid sequence as set forth in SEQ ID NO 3.

Another object of the present invention is to provide a method for at least reducing the levels of colonization by at least one target bacteria in an animal by administering to the animal a therapeutic composition comprising a bacteriocin produced by a novel strain of *Paenibacillus polymyxa* having the identifying characteristics of NRRL B-30507, NRRL B-30508, or NRRL B-30509; a novel strain of *Bacillus circulans* having the identifying characteristics of NRRL B-30644, and mixtures thereof.

Further objects and advantages of the invention will become apparent from the following description.

Deposit of the Microorganisms

*Paenibacillus polymyxa*, designated NRRL B-30507 (Strain 37), NRRL B-30508 (Strain 119), and NRRL B-30509 (Strain 602); and *Bacillus circulans* designated NRRL B-30644 have been deposited under the provisions of the Budapest Treaty on Aug. 3, 2001 for *P. polymyxa* NRRL B-30507, NRRL B-30508, and NRRL B-30509; and *B. circulans*, NRRL B-30644, was deposited on Apr. 1, 2003 with the U.S.D.A. Agricultural Research Service Patent Culture Collection (National Center for Agricultural Utilization Research, 1815 N. University Street, Peoria, Ill. 61604).

BRIEF DESCRIPTION OF THE DRAWINGS

FIG. 4 shows sequence alignment of mature class IIa bacteriocins including bacteriocin 37 (SEQ ID NO 1), bacteriocin 602 (SEQ ID NO 2), bacteriocin 1580 (SEQ ID NO 3), Lactococcin MMFII (SEQ ID NO 4), Mesentericin Y105 (SEQ ID NO 5), Leucocin A (SEQ ID NO 6), Bifidocin B (SEQ ID NO 7), Sakacin P (SEQ ID NO 8), Mundticin (SEQ ID NO 9), Sakacin A (SEQ ID NO 10), Pisciolin-126 (SEQ ID NO II), Carnobacteriocin BM1 (SEQ ID NO 12), Carnobacteriocin B2 (SEQ ID NO 13), Bavaricin MN (SEQ ID NO 14), Bacteriocin 31 (SEQ ID NO 15), Enterocin P (SEQ ID NO 16), Enterocin A (SEQ ID NO 17), Pediocin PA-1 (SEQ ID NO 18), Divercin V41 (SEQ ID NO 19), CoaA (SEQ ID NO 20), and Consenua (SEQ ID NO 21). The consensus sequence (Consenua) shows the residues conserved by at least 70% and when underlined, by more than 90%.

DETAILED DESCRIPTION OF THE INVENTION

Figure 1:
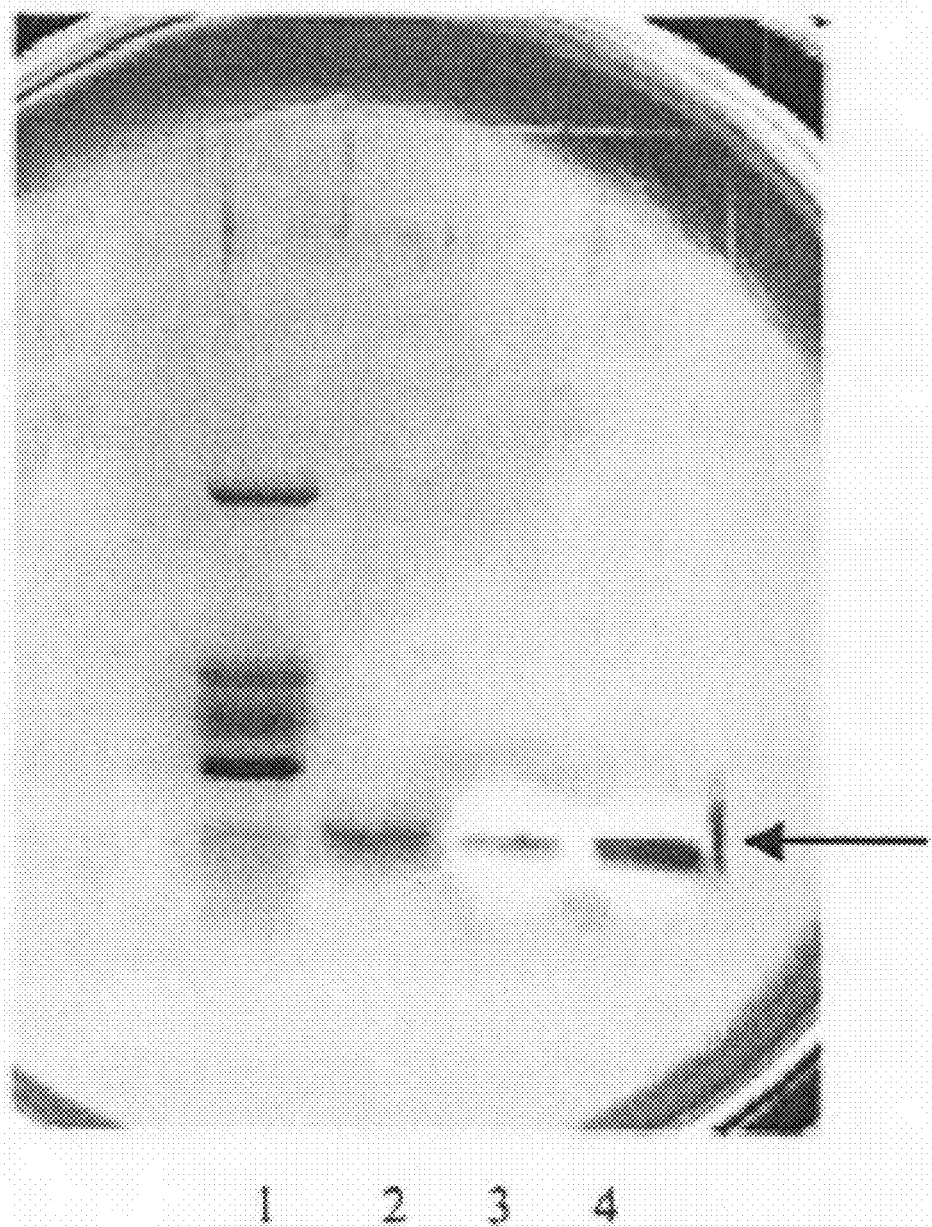
FIG. 1 is a photograph of gel overlaid with *Campylobacter jejuni* to determine which band or bands corresponds to the antimicrobial activity and molecular weight. Lane 1 shows molecular weight markers ranging from about 1,500 to about 27,000 (AMERSHAM PHARMACIA BIOTECH); 27,000, 20,000, 18,500, 6,000, 3,500, and 1,500 Da. The band in Lane 2 is insulin, the band in Lane 3 is pure bacteriocin 602 and the band in Lane 4 is pure bacteriocin 37. Lanes 3 and 4 corresponds to the antimicrobial activity, zone of growth inhibition (see arrow), and each had a mass of about 3,500 kDa. Other bands did not show antimicrobial activity.

The importance of enteric infections in humans has been increasingly well recognized. The relationship of poultry contamination and human infection has become well documented. The ability to diminish this health hazard by interventions at poultry processing plants is also well known. During broiler production and processing, fecal materials containing pathogens are transferred onto meat and persist in the food processing kitchens.

Metabolites of competing organisms may contribute to the control of pathogens such as *Campylobacter jejuni* and *Salmonella*. The novel antagonistic strains were isolated from cecal and crop mucosal surfaces of broilers. The native components of characterized antagonist are low molecular weight peptides, bacteriocins, which have a wide spectrum of antagonistic activity.

The present invention provides novel *Bacillus* and *Paenibacillus* strains, novel bacteriocins, amino acid sequences of said bacteriocins, therapeutic compositions containing the novel bacteriocins and/or strains producing them, and methods for using the novel therapeutic compositions.

The *Paenibacillus polymyxa* isolates are facultative anaerobes, gram-positive motile rods capable of growth at about 30, 37, and 42° C. The strains grow on nutrient agar or plate count agar, producing circular to irregular-shaped, low convex, grayish colonies with wavy margins that are about 2-3 mm in diameter after aerobic incubation for about 2-3 days at about 30° C. Colonies become white as cells sporulate. After about 48-72 hours incubation, ellipsoidal spores develop in non-swollen sporangia.

The *Bacillus circulans* isolate is a facultative anaerobe, gram-positive motile rods, and is capable of growth at about 30° C. or less. The strain grows on nutrient or plate count agar producing irregular-shaped edges. The colonies are about 2-5 mm in diameter after aerobic culture for about 2-3 days at about 30° C. After about 48-72 hours of incubation, ellipsoidal spores develop in non-swollen sporangia.

Screening of isolated *Paenibacillus* and *Bacillus* species for the production of bacteriocin activity is performed on nutrient agar on cultures seeded with different target bacteria of interest. Other test strains are cultured under aerobic conditions at about 37° C. for about 18-24 hours. *Yersinia enterocolitica* and *Y. pseudotuberculosis* are cultured at about 28° C. under aerobic conditions for about 18-24 hours. Tests for activity, against *Campylobacter jejuni* are performed on *C. jejuni* seeded *Campylobacter* agar containing about 5% lysed blood. The use of blood is well within the ordinary skill in the art and include for example, sheep, horse, etc. Tests for activity against *Campylobacter jejuni* is carried out under microaerobic conditions of about 5% $O_2$, about 10% $CO_2$, and about 85% $N_2$ for about 24-48 hours at about 42° C. Approximately 0.2 ml of the antagonistic bacteria suspended in normal saline is plated onto starch agar and incubated until spore formation which occurs after about 2-3 days of culture. Starch cubes of about 0.5 $cm^3$ are cut out and transferred onto *brucella* or *Campylobacter* agar supplemented with lysed blood, about 10 micrograms/ml rifampicin, about 2.4 U/ml of polymyxin, and seeded with about $10^7$ cells of *Campylobacter jejuni*. Plates are incubated at about 42° C. for approximately 24-48 hours under microaerobic conditions. Activity is evaluated by measuring zones of growth inhibition.

Isolates found to be antagonistic are evaluated for bacteriocin production. Crude antimicrobial preparations (CAPs) are prepared by ammonium sulfate precipitation only from cultures of antagonistic strains grown in modified Kugler's broth supplemented with about 0.03% alanine, about 0.045% tryptophan, and about 20% glucose, at about 32° C. for about 40 hours under aerobic conditions. The cultures are then centrifuged at about 2,500×g for about 10 minutes. Antagonistic peptides are isolated from supernatant by a combination of ammonium sulfate precipitation, CM-Sepharose, Superose, and Mono-Q-cation or anion exchange chromatography. Molecular weights of the peptides are determined by SDS-PAGE electrophoresis. pIs of the peptides are determined by isoelectric focusing. Amino acid sequences are determined by Edman degradation using, for example, a 491 cLC Automatic Sequencer (Applied Biosystems, Inc.).

For purposes of the present invention, the term "peptide" means a compound of at least two or more amino acids or amino acid analogs. The amino acids or amino acid analogs may be linked by peptide bonds. In another embodiment, the amino acids may be linked by other bonds, e.g., ester, ether, etc. Peptides can be in any structural configuration including linear, branched, or cyclic configurations. As used herein, the term "amino acids" refers to either natural or synthetic amino acids, including both the D or L optical isomers, and amino acid analogs.

Peptide derivatives and analogs of the present invention include, but are not limited to, those containing, as a primary amino acid sequence, all or part of the amino acid sequence of the peptide including altered sequences in which functionally equivalent amino acid residues are substituted for residues within the sequence resulting in conservative amino acid substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to significantly affect apparent molecular weight as determined by polyacrylamide gel electrophoresis or isoelectric point. Non-conservative amino acid substitutions may also be introduced to substitute an amino acid with a particularly preferable property. For example, Cys may be introduced at a potential site for disulfide bridges with another Cys. Pro may be introduced because of its particularly planar structure.

The peptides of the present invention can be chemically synthesized. Synthetic peptides can be prepared using the well known techniques of solid phase, liquid phase, or peptide condensation techniques, or any combination thereof, and can include natural and/or synthetic amino acids. Amino acids used for peptide synthesis may be standard Boc ($N^\alpha$-amino protected $N^\alpha$-t-butyloxycarbonyl)amino acid resin with the standard deprotecting, neutralization, coupling, and wash protocols of the original solid phase procedure of Merrifield (J. Am. Chem. Soc, Volume 85, 2149-2154, 1963), or the base-labile $N^\alpha$-amino protected 9-fluorenylmethoxycarbonyl (Fmoc) amino acid (Carpino and Han, J. Org. Chem., Volume 37, 3403-3409, 1972). In addition, the method of the present invention can be used with other $N^\alpha$-protecting groups that are familiar to those skilled in the art. Solid phase peptide synthesis may be accomplished by techniques within the ordinary skill in the art (See for example Stewart and Young, Solid Phase Synthesis, Second Edition, Pierce Chemical Co., Rockford, Ill., 1984; Fields and Noble, Int. J. Pept. Protein Res., Volume 35, 161-214, 1990), or by using automated synthesizers.

In accordance with the present invention, the peptides and/or the novel bacterial strains can be administered in a therapeutically acceptable carrier topically, parenterally, transmucosally, such as for example, orally, nasally, or rectally, or transdermally. The peptides of the present invention can be modified if necessary to increase the ability of the peptide to cross cellular membranes such as by increasing the hydrophobic nature of the peptide, introducing the peptide as a conjugate to a carrier, such as a ligand to a specific receptor, etc.

The present invention also provides for conjugating a targeting molecule to a peptide of the invention. Targeting molecules for purposes of the present invention mean a molecule which when administered in vivo, localizes to a desired location or locations. In various embodiments of the present invention, the targeting molecule can be a peptide or protein, antibody, lectin, carbohydrate, or steroid. The targeting molecule can be a peptide ligand of a receptor on the target cell or an antibody such as a monoclonal antibody. To facilitate crosslinking the antibody can be reduced to two heavy and light chain heterodimers, or the F(ab')$_2$ fragment can be reduced, and crosslinked to the peptide via the reduced sulfhydryl.

Another aspect of the present invention is to provide therapeutic compositions. The compositions may be for oral, nasal, pulmonary administration, injection, etc. The therapeutic compositions include effective amounts of at least one bacteriocin of the present invention and their derivatives and/or at least one novel strain to at least reduce the levels of colonization by at least one target bacteria together with acceptable diluents, preservatives, solubilizers, emulsifiers, adjuvants, and/or carriers. Diluents can include buffers such as Tris-HCl, acetate, phosphate, for example; additives can include detergents and solubilizing agents such as Tween 80, Polysorbate 80, etc., for example; antioxidants include, for example, ascorbic acid, sodium metabisulfite, etc.; preservatives can include, for example, Thimersol, benzyl alcohol, etc.; and bulking substances such as lactose, mannitol, etc.

The therapeutic composition of the present invention can be incorporated into particulate preparation of polymeric compounds such as polyvinylpyrrolidone, polylactic acid, polyglycolic acid, etc., or into liposomes. Liposomal encapsulation includes encapsulation by various polymers. A wide variety of polymeric carriers may be utilized to contain and/or deliver one or more of the therapeutic agents discussed above, including for example both biodegradable and nonbiodegradable compositions. Representative examples of biodegradable compositions include albumin, collagen, gelatin, hyaluronic acid, starch, cellulose (methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly (D,L-lactide-co-glycolide), poly(glycolide), poly(hydroxybutyrate), poly(alkylcarbonate) and poly (orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Ilium, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

Representative examples of nondegradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polypropylene, polyamides (nylon 6,6), polyurethane, poly(ester urethanes), poly(ether urethanes), poly(ester-urea), polyethers (poly(ethylene Oxide), poly(propylene oxide), Pluronics and poly(tetramethylene glycol)), silicone rubbers and vinyl polymers such as polyvinylpyrrolidone, poly(vinyl alcohol), poly(vinyl acetate phthalate). Polymers may also be developed which are either anionic (e.g., alginate, carrageenin, carboxymethyl cellulose and poly(acrylic acid), or cationic (e.g., chitosan, poly-L-lysine, polyethylenimine, and poly(allyl amine)) (see generally, Dunn et al., J. Applied Polymer Sci. 50:353-365, 1993; Cascone et al., J. Materials Sci.: Materials in Medicine 5:770-774, 1994; Shiraishi et al., Biol. Pharm. Bull. 16(11):1164-

1168, 1993; Thacharodi and Rao, Int'l J. Pharm. 120:115-118, 1995; Miyazaki et al., Int'l J. Pharm. 118:257-263, 1995).

Polymeric carriers can be fashioned in a variety of forms, with desired release characteristics and/or with specific desired properties. For example, polymeric carriers may be fashioned to release a therapeutic agent upon exposure to a specific triggering event such as pH (see e.g., Heller et al., "Chemically Self-Regulated Drug Delivery Systems," in Polymers in Medicine III, Elsevier Science Publishers B. V., Amsterdam, 1988, pp. 175-188; Kang et al., J. Applied Polymer Sci. 48:343-354, 1993; Dong et al., J. Controlled Release 19:171-178, 1992; Dong and Hoffman, J. Controlled Release 15:141-152, 1991; Kim et al., J. Controlled Release 28:143-152, 1994; Cornejo-Bravo et al., J. Controlled Release 33:223-229, 1995; Wu and Lee, Pharm. Res. 10(10):1544-1547, 1993; Serres et al., Pharm. Res. 13(2):196-201, 1996; Peppas, "Fundamentals of pH- and Temperature-Sensitive Delivery Systems," in Gurny et al. (eds.), Pulsatile Drug Delivery, Wissenschaftliche Verlagsgesellschaft mbH, Stuttgart, 1993, pp. 41-55; Doelker, "Cellulose Derivatives," 1993, in Peppas and Langer (eds.), Biopolymers I, Springer-Verlag, Berlin). Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers, can be fashioned which are temperature sensitive (see e.g., Chen et al., "Novel Hydrogels of a Temperature-Sensitive Pluronic Grafted to a Bioadhesive Polyacrylic Acid Backbone for Vaginal Drug Delivery," in Proceed. Intern. Symp. Control. Rel. Bioact. Mater. 22:167-168, Controlled Release Society, Inc., 1995; Okano, "Molecular Design of Stimuli-Responsive Hydrogels for Temporal Controlled Drug Delivery," in Proceed. Intern. Symp. Control. Rel. Bioact. Mater. 22:111-112, Controlled Release Society, Inc., 1995; Johnston et al., Pharm. Res. 9(3):425-433, 1992; Tung, Int'l J. Pharm. 107:85-90, 1994; Harsh and Gehrke, J. Controlled Release 17:175-186, 1991; Bae et al., Pharm. Res. 8(4):531-537, 1991; Dinarvand and D'Emanuele, J. Controlled Release 36:221-227, 1995; Yu and Grainger, "Novel Thermos-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820-821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822-823; Hoffman et al., "Characterizing Pore Sizes and Water "Structure" in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829-830; Kim et al., Pharm. Res. 9(3):283-290, 1992; Bae et al., Pharm. Res. 8(5):624-628, 1991; Kono et al., J. Controlled Release 30:69-75, 1994; Yoshida et al., J. Controlled Release 32:97-102, 1994; Okano et al., J. Controlled Release 36:125-133, 1995; Chun and Kim, J. Controlled Release 38:39-47, 1996; D'Emanuele and Dinarvand, Int'l J. Pharm. 118:237-242, 1995; Katono et al., J. Controlled Release 16:215-228, 1991; Hoffman, "Thermally Reversible Hydrogels Containing Biologically Active Species," in Migliaresi et al. (eds.), Polymers in Medicine III, Elsevier Science Publishers B. V., Amsterdam, 1988, pp. 161-167; Hoffman, "Applications of Thermally Reversible Polymers and Hydrogels in Therapeutics and Diagnostics," in Third International Symposium on Recent Advances in Drug Delivery Systems, Salt Lake City, Utah, Feb. 24-27, 1987, pp. 297-305; Gutowska et al., J. Controlled Release 22:95-104, 1992; Palasis and Gehrke, J. Controlled Release 18:1-12, 1992; Paavola et al., Pharm. Res. 12(12):1997-2002, 1995).

Representative examples of thermogelling polymers, and their gelatin temperature (LCST (.degree.C.)) include homopolymers such as poly(N-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly(N, n-diethylacrylamide), 32.0; poly(N-isopropylmethacrylamide), 44.0; poly (N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide). Other representative examples of thermogelling polymers include cellulose ether derivatives such as hydroxypropyl cellulose, 41.degree.C.; methyl cellulose, 55.degree.C.; hydroxypropylmethyl cellulose, 66.degree.C.; and ethylhydroxyethyl cellulose, and Pluronics such as F-127, 10-15.degree.C.; L-122, 19.degree.C.; L-92, 26.degree. C.; L-81, 20.degree.C.; and L-61, 24.degree.C.

A wide variety of forms may be fashioned by the polymeric carriers of the present invention, including for example, rod-shaped devices, pellets, slabs, or capsules (see e.g., Goodell et al., Am. J. Hosp. Pharm. 43:1454-1461, 1986; Langer et al., "Controlled release of macromolecules from polymers", in Biomedical Polymers, Polymeric Materials and Pharmaceuticals for Biomedical Use, Goldberg, E. P., Nakagim, A. (eds.) Academic Press, pp. 113-137, 1980; Rhine et al., J. Pharm. Sci. 69:265-270, 1980; Brown et al., J. Pharm. Sci. 72:1181-1185, 1983; and Bawa et al., J. Controlled Release 1:259-267, 1985).

Therapeutic agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, threads of various size, films and sprays.

Another aspect of the present invention is to provide a therapeutic composition and animal feed. The therapeutic composition of the present invention can be encapsulated using a polymeric carrier as described above and then added to a feed by any known means of applying it to feed such as for example, by mechanical mixing, spraying, etc. The therapeutic composition includes, for example, an amount of at least one bacteriocin effective to at least reduce the levels of colonization by at least one target bacteria in an animal, such as for example approximately 0.5 grams of bacteriocin(s)/100 grams, approximately 1.25 grams of a polymeric carrier such as polyvinylpyrrolidone/100 grams, and about 8.6% of a diluent such as water/100 grams mixed with any granular component that is digest able, such as for example, milled maize grain; ground grains such as for example oats, wheat, buckwheat; ground fruits such as for example, pears, etc. The therapeutic composition is then added to any type of animal feed in amounts effective to at least reduce the levels of colonization of at least one target bacteria such as for example in ratios of bacteriocin to feed of about 1:10 to about 1:100. For purposes of the present invention, examples of animal feed include green foder, silages, dried green fodder, roots, tubers, fleshy fruits, grains, seeds, brewer's grains, pomace, brewer's yeast, distillation residues, milling byproducts, byproducts of the production of sugar, starch or oil production, and various food wastes. The product can be added to the animal feedstuffs for cattle, poultry, rabbit, pig, or sheep rearing, etc. It can be used mixed with other feed additives for these stock.

The following examples are intended only to further illustrate the invention and are not intended to limit the scope of the invention as defined by the claims.

Example 1

Five novel antagonistic strains, *Paenibacillus polymyxa* strains 37 (NRRL B-30507), 114, 119 (NRRL B-30508), 592, and 602 (NRRL B-30509), producing bacteriocins were isolated from mucous surfaces of about 1.0 grams of the cecal and crop of broilers which was suspended in about 10 ml of sterile 0.85% w/v saline solution (normal saline) and heated at about 80° C. for about 15 minutes. *Bacillus circulans* 1580 (NRRL B-30644) was isolated from soil as above. Approximately 0.10 ml of about 1:50, and 1:2,500 suspensions was spread plated onto either plate count agar or Starch Agar. Plates were incubated at about 30° C. for about 24 hours and about 72 hours under aerobic conditions. Colonies with different morphology were streaked onto Starch agar. These cultures were incubated under aerobic conditions for about 72 hours at about 30° C.

Strains 37, 114, 119, 592, and 602 were grown at about 30° C. for about 24 hours on Starch Agar. They are facultative anaerobes, Gram-positive motile rods capable of growth at about 30, 37, and 42° C. The organisms grow on nutrient agar or plate count, agar producing circular to irregular-shaped, low convex, grayish colonies with relatively wavy margins that are about 2-3 mm in diameter after aerobic incubation for about 2-3 days, at about 30° C. Colonies become white as cells sporulate. After about 48-72 hours incubation, ellipsoidal spores developed in non-swollen sporangia.

*Bacillus circulans* strain 1580 was grown at about 30° C. for about 24 hours on Starch agar. It is Gram-positive, facultative anaerobe, motile rods, and capable of growth at 30° C. or less. The organism grows on nutrient agar or plate count, agar producing irregular-shaped, low convex, white colonies with very irregular edges. The colonies are about 2-5 mm in diameter after aerobic culture for about 2-3 days at about 30° C. After about 48-72 hours incubation, ellipsoidal spores developed in non-swollen sporangia. Voges-Prbskauer reaction is positive for strains 37, 114, 119, 592, and 602 but not for strain 1580. Citrate is not utilized, gelatin is hydrolyzed, nitrate is not reduced for all the strains as determined with API 20E strips.

The results in the API 50CH galleries, when API CHB suspension medium is used are present below in Table 1. Table 2 (below) results indicate that strains 37, 114, 119, and 602 are most likely to be *Paenibacillus polymyxa*, strain 592 as *Bacillus pumilus* and strain 1580 as *Bacillus circulans*.

Target bacteria for assessing antagonistic activity of antagonistic isolates from strains 37, 114, 119, 592, and 602, included four isolates of *Campylobacter jejuni* (*C. jejuni*) isolated from broilers in Russia and strain ATCC 11168, several species from the family of Enterobacteriaceae, *Pseudomonas aeruginosa* strain ATCC 9027, *Staphylococcus aureus*, and *Listeria monocytogenes*. Cultures of *C. jejuni* were grown either on *brucella* agar or *Campylobacter* agar containing about 5% partially lysed blood at about 42° C. for approximately 24-48 hours under microaerobic conditions of about 5% $O_2$, about 10% $CO_2$, and about 85% $N_2$. The other strains were cultured on nutrient agar at about 37° C. or about 28° C. for *Y. enterocolitica* and *Y. pseudotuberculosis* for about 18-24 hours under aerobic conditions. Antagonistic activity of the isolates against *Campylobacter* was evaluated. Approximately 0.2 ml of the suspensions in normal saline was plated onto starch agar and incubated at about 30° C. for about 2-3 days until spore formation. Starch agar cubes of about 0.5 $cm^3$ were cut out and transferred onto *brucella* agar or *Campylobacter* agar supplemented with about 5%-10% partially lysed blood, about 10 micrograms/ml rifampicin, and about 2.5 u/ml of polymyxin and inoculated with approximately $10^7$ cells of *Campylobacter jejuni* per plate. Plates were incubated at about 42° C. for approximately 24 to 48 hours under microaerobic conditions as described above. Antagonistic activity was evaluated by measuring the size of the diameter of the zones of *C. jejuni* inhibition.

Antagonistic activity to *Campylobacter jejuni* was evaluated using 365 isolates. Out of these, 56 isolates exhibited antagonism to *C. jejuni*. The 15 most antagonistic isolates were used in tests against other microorganisms (Tables 3 and 4 below). Isolates 37, 114, 119, 592, and 602 manifested the widest spectrum of antagonistic activity and differed from one another in their growth characteristics and ability to lyse erythrocytes. These 6 strains were identified as *Bacillus* spp.-like organisms according to system API 50CH and API 20E (Biomerieux, France).

TABLE 1

API 50 CH results when API CHB suspension medium is used.

| Strains | API Score | *Bacillus* Species |
|---|---|---|
| 37 | 98 | *Paenibacillus polymyxa* |
| 114 | 99 | *Paenibacillus polymyxa* |
| 119 | 98 | *Paenibacillus polymyxa* |
| 592 | 99.9 | *Bacillus pumilus* |
| 602 | 99.5 | *Paenibacillus polymyxa* |
| 1580 | 99.9 | *Bacillus circulans* 2 |

TABLE 2

Characterization of Strains

| Carbohydrates | 37 | 114 | 119 | 592 | 602 | 1580 |
|---|---|---|---|---|---|---|
| Glycerol | † | † | † | † | † | – |
| Erythritol | – | – | – | – | – | – |
| D-Arabinose | – | – | – | – | – | – |
| L-Arabinose | | † | † | † | † | † |
| Ribose | † | † | † | † | † | † |
| D-Xylose | † | † | † | † | † | †/– |
| L-Xylose | – | – | – | – | – | – |
| Adonitol | – | – | – | – | – | – |
| β-Methyl-xyloside | † | – | † | – | † | † |
| Galactose | † | † | † | †/– | †/– | †/– |

TABLE 2-continued Characterization of Strains

| Carbohydrates | 37 | 114 | 119 | 592 | 602 | 1580 |
|---|---|---|---|---|---|---|
| D-Glucose | † | † | † | † | † | † |
| D-Fructose | † | † | † | † | † | † |
| D-Mannose | † | † | † | † | † | † |
| L-Sorbose | – | – | – | – | – | – |
| Rhamnose | – | – | – | – | – | – |
| Dulcitol | – | – | – | – | – | – |
| Inositol | – | – | – | – | – | – |
| Mannitol | † | † | † | † | † | † |
| Sorbitol | – | – | – | – | – | – |
| a Methyl-D-mannoside | – | – | – | – | – | † |
| a Methyl-D-glucoside | † | † | † | † | † | – |
| N-Acetyl-glucosamine | – | – | – | – | – | – |
| Amygdaline | † | †/– | † | † | †/– | † |
| Arbutine | † | † | † | † | † | † |
| Esculine | † | † | † | † | † | † |
| Salicine | † | † | † | † | † | † |
| Cellobiose | † | † | † | † | † | † |
| Maltose | † | † | † | † | † | † |
| Lactose | † | †/– | † | – | † | † |
| Melibiose | †/– | † | † | – | † | † |
| Saccharose | † | † | † | † | † | † |
| Trehalose | † | † | † | † | † | † |
| Inulin | †/– | – | – | – | – | † |
| Melezitoze | – | – | – | – | – | – |
| D-Raffinose | † | † | † | – | † | † |
| Amidon | † | † | † | – | † | † |
| Glycogene | † | † | † | – | † | † |
| Xylitol | – | – | – | – | – | – |
| βGentibiose | – | – | – | †/– | †/– | † |
| D-Turanose | – | – | – | – | † | – |
| D-Lyxose | – | – | – | – | – | – |
| D-Tagatose | – | – | – | †/– | – | – |
| D-Fucose | – | – | – | – | – | – |
| L-Fucose | – | – | – | – | – | – |
| D-Arabitol | – | – | – | – | – | – |
| Gluconate | – | – | – | – | – | – |
| 2-ceto-Gluconate | – | – | – | – | – | – |
| 5-ceto-Gluconate | – | – | – | – | – | – |

TABLE 3

Inhibitory activity of isolates against test strains of *Campylobacter jejuni*.

| Antagonistic Identification | Source of Strain | Diameter (mm) of growth inhibition of *C. jejuni* | | | | | Hemolytic Activity |
|---|---|---|---|---|---|---|---|
| | | 11168 | B1 | L4 | F2 | KI | |
| 37 | broiler, crop | 5 | 3 | 4 | 5 | 4 | – |
| 114 | broiler, intestine | 6 | 5 | 5 | 5 | 5 | – |
| 119 | broiler, intestine | 4 | 3 | 5 | 5 | 6 | – |
| 236 | broiler, intestine | 2 | 2 | 3 | 3 | 4 | +/– |
| 265 | broiler, intestine | 2 | 2 | 2 | 4 | 6 | + |
| 346 | broiler, crop | 3 | 5 | 3 | 3 | 6 | +/– |
| 358 | broiler, crop | 3 | 3 | 3 | 4 | 5 | + |
| 361 | broiler, crop | 3 | 3 | 3 | 2 | 4 | + |
| 362 | broiler, crop | 4 | 4 | 4 | 3 | 5 | + |
| 397 | broiler, intestine | 4 | 5 | 3 | 4 | 6 | + |
| 442 | quail, intestine | 4 | 3 | 4 | 4 | 4 | + |
| 462 | quail, intestine | 3 | 5 | 4 | 4 | 5 | + |
| 538 | broiler, crop | 4 | 5 | 5 | 4 | 5 | + |
| 592 | broiler, crop | 5 | 5 | 4 | 4 | 5 | +/– |
| 602 | broiler, crop | 6 | 5 | 5 | 5 | 6 | – |

(+) = presence of activity;
(+/–) = weak activity;
(–) = no activity

TABLE 4

Inhibitory activity against designated species of microorganisms.

| | Diameter (mm) of growth inhibition | | | | | | | | | | | | |
|---|---|---|---|---|---|---|---|---|---|---|---|---|---|
| Indicating Strains | 37 | 114 | 119 | 236 | 265 | 346 | 361 | 397 | 442 | 462 | 538 | 592 | 602 |
| *S. enteritidis* 4 | 1 | 3 | 9 | 0 | 0 | 0 | 0 | 2 | 0 | 0 | 0 | 4 | 6 |
| *S. enteritidis* 204 | 1 | 2 | 7 | 0 | 0 | 0 | 0 | 2 | 0 | 0 | 0 | 3 | 5 |
| *S. enteritidis* 237 | 1 | 2 | 9 | 0 | 0 | 0 | 0 | 2 | 0 | 0 | 0 | 3 | 4 |
| *S. choleraesuis* 434/4 | 2 | 3 | 9 | 0 | 0 | 0 | 0 | 2 | 0 | 0 | 0 | 4 | 7 |
| *S. choleraesuis* 320 | 2 | 3 | 9 | 0 | 0 | 0 | 0 | 2 | 0 | 0 | 0 | 3 | 6 |
| *S. typhimurium* 383/60 | 1 | 2 | 6 | 0 | 0 | 0 | 0 | 0 | 0 | 0 | 0 | 3 | 4 |
| *S. gallinarum pullorum* | 0 | 2 | 8 | 0 | 0 | 0 | 0 | 0 | 0 | 0 | 0 | 5 | 5 |
| *E. coli* 0157: H7Y61 | 2 | 3 | 10 | 0 | 0 | 0 | 0 | 2 | 0 | 0 | 0 | 3 | 5 |
| *E. coli* 0157: H7131 | 1 | 2 | 9 | 0 | 0 | 0 | 0 | 2 | 0 | 0 | 0 | 3 | 5 |
| *E. coli* EDL933 | 2 | 2 | 7 | 0 | 0 | 0 | 0 | 2 | 0 | 0 | 0 | 5 | 6 |
| *Y. enterocolitica* 03 | 0 | 2 | 0 | 0 | 0 | 0 | 0 | 0 | 0 | 0 | 0 | 2 | 3 |
| *Y. enterocolitica* 09 | 0 | 1 | 0 | 0 | 0 | 0 | 0 | 0 | 0 | 0 | 0 | 2 | 3 |
| *Citrobacter freundii* | 0 | 2 | 5 | 0 | 0 | 0 | 0 | 0 | 0 | 0 | 0 | 3 | 3 |
| *Klebsiella pneumoniae* | 2 | 2 | 4 | 0 | 0 | 0 | 0 | 0 | 0 | 0 | 0 | 3 | 4 |
| *Sh. dysenteriae* | 0 | 0 | 0 | 2 | 0 | 3 | 2 | 3 | 2 | 0 | 0 | 0 | 0 |
| *Staphylococcus aureus* | 6 | 5 | 0 | 3 | 0 | 5 | 3 | 5 | 0 | 0 | 0 | 3 | 1 |

TABLE 4-continued

Inhibitory activity against designated species of microorganisms.

Diameter (mm) of growth inhibition

| Indicating Strains | 37 | 114 | 119 | 236 | 265 | 346 | 361 | 397 | 442 | 462 | 538 | 592 | 602 |
|---|---|---|---|---|---|---|---|---|---|---|---|---|---|
| *Y. pseudotuberculosis* 4 | 0 | 2 | 5 | 0 | 0 | 0 | 0 | 0 | 0 | 0 | 0 | 3 | 4 |
| *Y. pseudotuberculosis* 14 | 0 | 1 | 5 | 0 | 0 | 0 | 0 | 0 | 0 | 0 | 0 | 3 | 5 |
| *Pseudomonas aeruginosa* ATCC9027 | 3 | 3 | 5 | 0 | 0 | 0 | 0 | 0 | 0 | 0 | 0 | 2 | 4 |
| *Proteus mirabilis* | 2 | 3 | 0 | 4 | 0 | 7 | 4 | 3 | 3 | 0 | 0 | 0 | 0 |
| *Morganella morganii* | 0 | 0 | 0 | 0 | 0 | 0 | 0 | 0 | 0 | 0 | 0 | 0 | 0 |
| *L. monocytogenes* 9-72 | 3 | 3 | 3 | 0 | 0 | 0 | 0 | 0 | 0 | 0 | 0 | 2 | 4 |
| *L. monocytogenes* A | 3 | 3 | 2 | 0 | 0 | 0 | 0 | 0 | 0 | 0 | 0 | 2 | 4 |

Example 2

Crude, antimicrobial preparations were extracted from cultures of 14 different antagonistic strains. Antagonists were grown in about 250 ml of modified poor Kugler's broth medium (Kugler et al. Archives of Microbiology, Volume 153, 276-281, 1990; herein incorporated by reference) supplemented with about 0.03% alanine, about 0.045% tryptophan, and about 20% glucose, at about 32° C. for about 40 hours under aerobic conditions. The resulting cultures were centrifuged at approximately 2,500×g for about 10 minutes, removing most of the viable cells. The decanted supernatant was mixed with about 80% saturated ammonium sulfate and incubated at about 4° C. for about 24 hours to precipitate the bacteriocin compounds. Following centrifugation at approximately 10,000×g for about 20 minutes, the sediment was resuspended in approximately 1.5 ml of about 10 mM phosphate sodium buffer, pH about 7.0, and dialyzed overnight against approximately 2.5 Liters of the same buffer. The solution was designated a crude antimicrobial preparation (CAP). Each sample of the preparation was sterilized by passing through a 0.22 micron-pore filter (Millipore, Bedford, Mass., USDA).

Example 3

The spectrum of antimicrobial activity of the CAPs was determined using a spot test. Approximately 1 ml of sterile crude antimicrobial preparations (CAP), obtained as in Example 2 above, were diluted with approximately 1 ml of phosphate-sodium buffer (pH about 7.0) and sterilized as above in Example 2. Approximately 10 microliters of each sample were plated onto blood-supplemented *Campylobacter* agar or Nutrient agar (MPA or Meta Peptone Agar) previously seeded with cells of target bacteria. Plates containing cultures of *C. jejuni* were grown at about 42° C. under microaerobic conditions, *Y. enterocolitica* and *Y. pseudotuberculosis* were cultured aerobically at about 28° C., and other bacterial strains were incubated aerobically at about 37° C. for about 24 or 48 hours. Identification was based on inhibition areas produced by the target bacteria. Activity of CAP was expressed in arbitrary units (AU) per one milliliter of the preparation at which a visible zone of inhibition of the growth of culture appears (Henderson et al., Archives of Biochemistry and Biophysics, Volume 295, 5-12, 1992; herein incorporated by reference). All experiments were conducted in duplicate.

Tables 5 and 6 below show the antagonistic activity of the crude antimicrobial preparations, prepared as described above in example 2, against strains of microorganisms. Table 5 is directed to activity against four strains of *C. jejuni*-ATCC 11168, F2, L4, and B1. Preparations from strains 37, 114, 119, 602, and 1580 were most effective. Table 6 is directed to activity against many strains of bacteria. Crude antimicrobial preparations of isolates 37, 114, 119, 592, and 602 were most effective against the target cultures. These preparations inhibited the growth of all tested Gram-negative and Gram-positive target bacteria except for *Morganella morganii*.

Table 7 (below) shows the activity of the most effective CAPs from strains 37, 602, and 1580 against a variety of bacterial strains. Again, these results show that CAPs from strains 37, 602, and 1580 inhibited growth of all tested Gram-negative and Gram-positive target bacteria except for *Morganella morganii*.

TABLE 5

Anti-*Campylobacter jejuni* activity of crude antimicrobial preparations (CAPs).

| *C. jejuni* strains | Activity of CAP (AU/ml) | | | | | | | | | | | | | |
|---|---|---|---|---|---|---|---|---|---|---|---|---|---|---|
| | 37 | 114 | 119 | 236 | 265 | 346 | 361 | 397 | 442 | 462 | 538 | 592 | 602 | 1580 |
| ATCC 11168 | 12800 | 12800 | 6400 | 3200 | 1600 | 3200 | 800 | 800 | 800 | 1600 | 3200 | 3200 | 6400 | 12800 |
| F-2 | 12800 | 12800 | 6400 | 1600 | 1600 | 3200 | 800 | 400 | 400 | 1600 | 1600 | 6400 | 6400 | 12800 |
| L-4 | 12800 | 12800 | 6400 | 3200 | 1600 | 800 | 400 | 400 | 800 | 400 | 1600 | 3200 | 6400 | 12800 |
| B-1 | 12800 | 12800 | 6400 | 3200 | 1600 | 800 | 200 | 200 | 200 | 400 | 3200 | 6400 | 6400 | 12800 |

TABLE 6

Antibacterial activity of crude antimicrobial preparations (CAPs).

Activity of CAPs by designated strains (dilution 1:8) (zone of inhibition diameter, mm)

| Challenged Bacterial Strains | 37 | 114 | 119 | 236 | 265 | 346 | 361 | 397 | 442 | 462 | 538 | 592 | 602 |
|---|---|---|---|---|---|---|---|---|---|---|---|---|---|
| S. enteritidis 4 | 20 | 20 | 20 | 12 | 14 | 25 | — | 24 | — | 14 | 18 | 20 | 21 |
| S. enteritidis 204 | 25 | 25 | 20 | 10 | 14 | — | 12 | 8 | — | — | 21 | 25 | 27 |
| S. enteritidis 237 | 25 | 25 | 20 | 10 | 14 | — | 12 | 8 | — | — | 21 | 25 | 27 |
| S. typhimurium 264/1 | 20 | 20 | 25 | 12 | 15 | — | 30 | 8 | 4 | 17 | 20 | 20 | 21 |
| S. choleraesuis 434/1 | >50 | >50 | >50 | >50 | >50 | >50 | 29 | 15 | — | 18 | 30 | >50 | >50 |
| S. gallinarum pullorum | 25 | 25 | 21 | 10 | 20 | — | 18 | 7 | — | 18 | 21 | 22 | 21 |
| E. coli 0157:H7 904 | 20 | 20 | 20 | — | 18 | — | 24 | 24 | 14 | 19 | 20 | 20 | 20 |
| E. coli EDL933 | 25 | 25 | 25 | 15 | 18 | — | 35 | — | 28 | — | 8 | 14 | 21 |
| Y. enterocolitica 03 | 30 | 30 | 30 | 15 | 20 | — | 3 | 20 | — | 20 | 14 | 20 | 30 |
| Y. enterocolitica 09 | 30 | 30 | 25 | — | 15 | — | 20 | — | 14 | — | 20 | 17 | 32 |
| Y. enterocolitica 11 | 25 | 25 | 25 | 12 | 22 | — | 14 | — | 11 | 10 | 20 | 11 | 14 |
| Staphylococcus epidermitidis 4 | 27 | 27 | 28 | 20 | 20 | 18 | 32 | 10 | 14 | 20 | 30 | 20 | 14 |
| Staphylococcus aureus | 30 | 30 | 30 | 20 | 20 | 15 | 50 | 30 | >50 | >50 | 30 | 21 | 16 |
| Citrobacter freundii | 14 | 14 | 22 | — | — | — | 12 | — | — | — | 18 | 14 | 18 |
| Klebsiella pneumoniae | 29 | 29 | 30 | — | 28 | — | 12 | — | — | — | 14 | 18 | 20 |
| Y. pseudotuberculosis 914 | 28 | 28 | 28 | — | — | — | — | — | — | — | 10 | 23 | 21 |
| SH. dysenteriae | 28 | 28 | 32 | 28 | 20 | — | 24 | 14 | — | — | 22 | 28 | 28 |
| Pseudomonas aeruginosa | 20 | 20 | — | — | — | — | — | — | — | — | — | 20 | 21 |
| Proteus mirabilis | 13 | 13 | 15 | — | — | — | — | — | — | — | 11 | 10 | 12 |
| Morganella morganii | — | — | — | — | — | — | — | — | — | — | — | — | — |
| L. monocytogenes 9-72 | 24 | 24 | 30 | — | — | — | — | — | — | — | 21 | 25 | 23 |

TABLE 7

Activity of Bacillus isolates-produced CAPs as evaluated in spot-test. Activity of CAPs AU/ml.

| Test strains | 37 | 602 | 1580 |
|---|---|---|---|
| S. enteritidis 4 | 6,400 | 3,200 | 6,400 |
| S. enteritidis 204 | 6,400 | 3,200 | 6,400 |
| S. enteritidis 237 | 6,400 | 3,200 | 12,800 |
| S. typhimurium 264/1 | 3,200 | 3,200 | 6,400 |
| S. choleraesuis 434/1 | 3,200 | 3,200 | 6,400 |
| S. gallinarum pullorum | 800 | 400 | 1,600 |
| E. coli O157:H7 904 | 12,800 | 3,200 | 6,400 |
| E. coli EDL 933 | 12,000 | 6,400 | 12,800 |
| Y. enterocolitica 03 | 1,600 | 800 | 3,200 |
| Y. enterocolitica 09 | 1,600 | 800 | 3,200 |
| Y. enterocolitica 11 | 400 | 400 | 800 |
| Staphylococcus epidermitidis 4 | 6,400 | 6,400 | 12,800 |
| Staphylococcus aureus | 3,200 | 3,200 | 3,200 |
| Citrobacter freundii | 6,400 | 6,400 | 6,400 |
| Klebsiella pneumoniae | 3,200 | 1,600 | 6,400 |
| Y. pseudotuberculosis 914 | 400 | — | 800 |
| Sh. dysenteriae | 400 | 400 | 800 |
| Pseudomonas aeruginosa | 800 | 800 | 800 |
| Proteus mirabilis | 400 | — | 800 |
| Morganella morganii | — | — | 800 |
| L. monocytogenes 9-72 | 3,200 | 3,200 | 6,400 |

Example 4

CAPs and bacteriocins were electrophoresed in about 15% agarose gel weight, about 1% SDS (9×12 cm) in Tri-glycine buffer. After electrophoresis at about 100 mA for approximately 4 hours, gels were fixed with a solution containing approximately 15% ethanol and approximately 1% acetic acid. The gels were then washed with distilled water for approximately 4 hours. To determine molecular weights of protein fractions, the gel was stained with a solution containing approximately 0.21% Coomassie Blue G-250, about 40% ethanol, and about 7% acetic acid. Washed gels were tested against three target bacteria, C. jejuni ATCC 11168, E. coli 0157:H7 904, and S. enteritidis 204 by the method of Bhunia et al. (Journal of Industrial Microbiology, Volume 2, 319-322, 1987; herein incorporated by reference). The gels were placed in Petri dishes, covered with 5% blood-semi-solid Campylobacter agar (about 0.75%) or semi-solid MPA, and seeded with cells of the test strains. Plates containing C. jejuni were incubated at about 42° C. for approximately 48 hours under microaerobic conditions, E. coli O157:H7 and S. enteriditidis at about 37° C. for approximately 24 hours. Assessment was based on visualization of zones of the inhibited growth of the test strains in the presence of bacteriocins. Activity of the purified bacteriocins was evaluated (Table 8 and FIG. 1).

Figure 2:
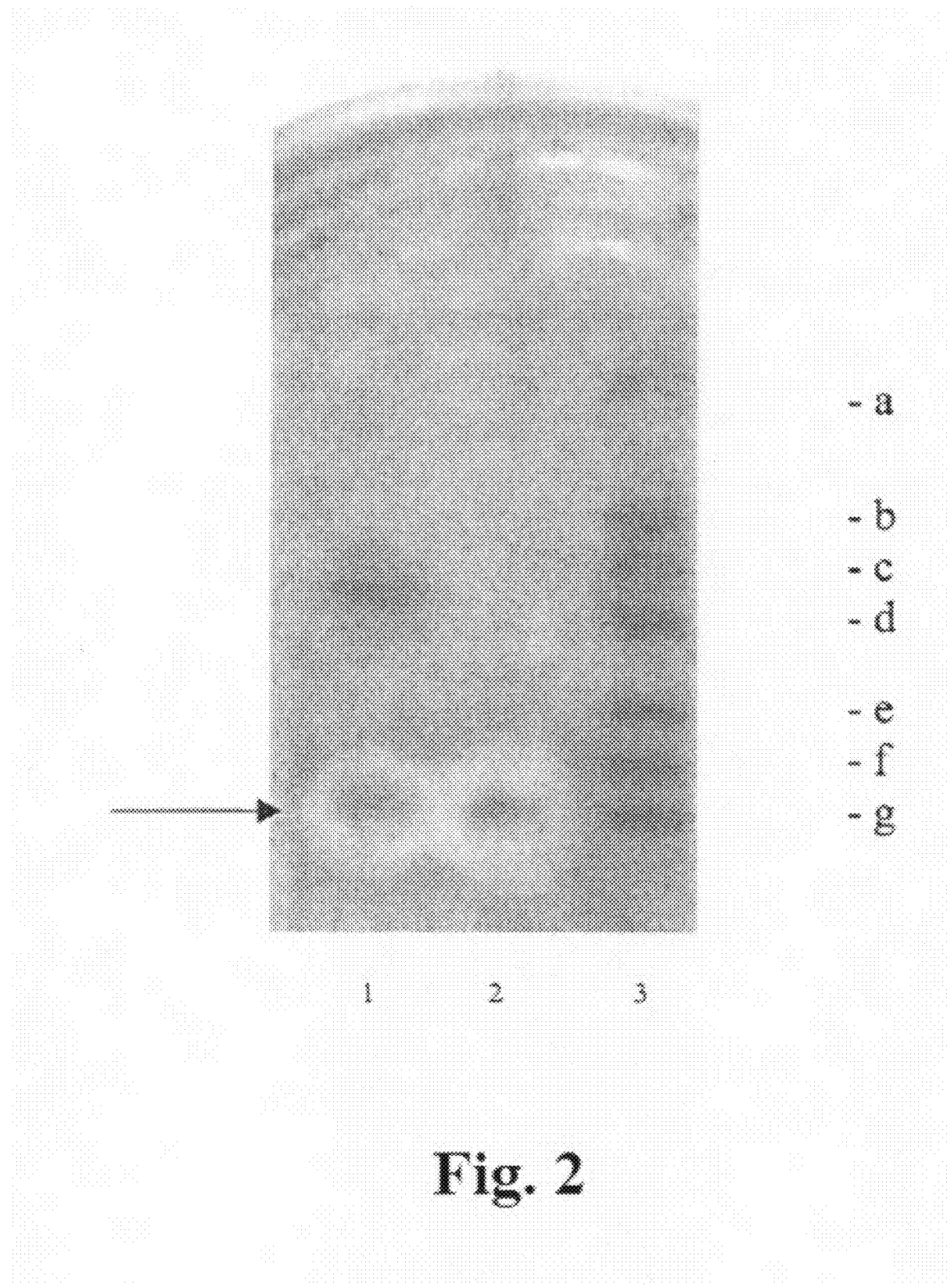
FIG. 2 is a photograph of a gel overlaid with *Campylobacter jejuni* to determine which band or bands of bacteriocin 37 corresponds to the antimicrobial activity and isoelectric point. Lane 3 contains pI standards (Protein test mixture 7, pI Marker Proteins, Serva): (a) 8.45, (b) 7.9, (c) 7.5, (d) 7.1, (e) 6.3, (f) 5.1, (g) 4.7. The band in Lane 1 (CAP 37) and the band in lane 2 (pure bacteriocin 37) corresponds to the antimicrobial activity, the zone of growth inhibition (see arrow), and a pI of about 4.8. Other bands did not show antimicrobial activity.

Isoelectrofocusing identified four distinct fractions which differed in isoelectric points (pI): CAP 37, 114, 119, and 592 each contained fractions with pI=about 4.8, about 7.3, about 9.2, and about 9.8. CAP 602 contained fractions with pI=about 5.0, about 7.2, about 8.9, and about 9.7. Antagonistic activity to C. jejuni was observed in the fraction with pI=about 4.8 in preparations 37, 114, 119, and 592; while in preparation 602 this inhibition was observed in the fraction with pI=about 7.2 (FIG. 2, Table 8, below).

Figure 3:
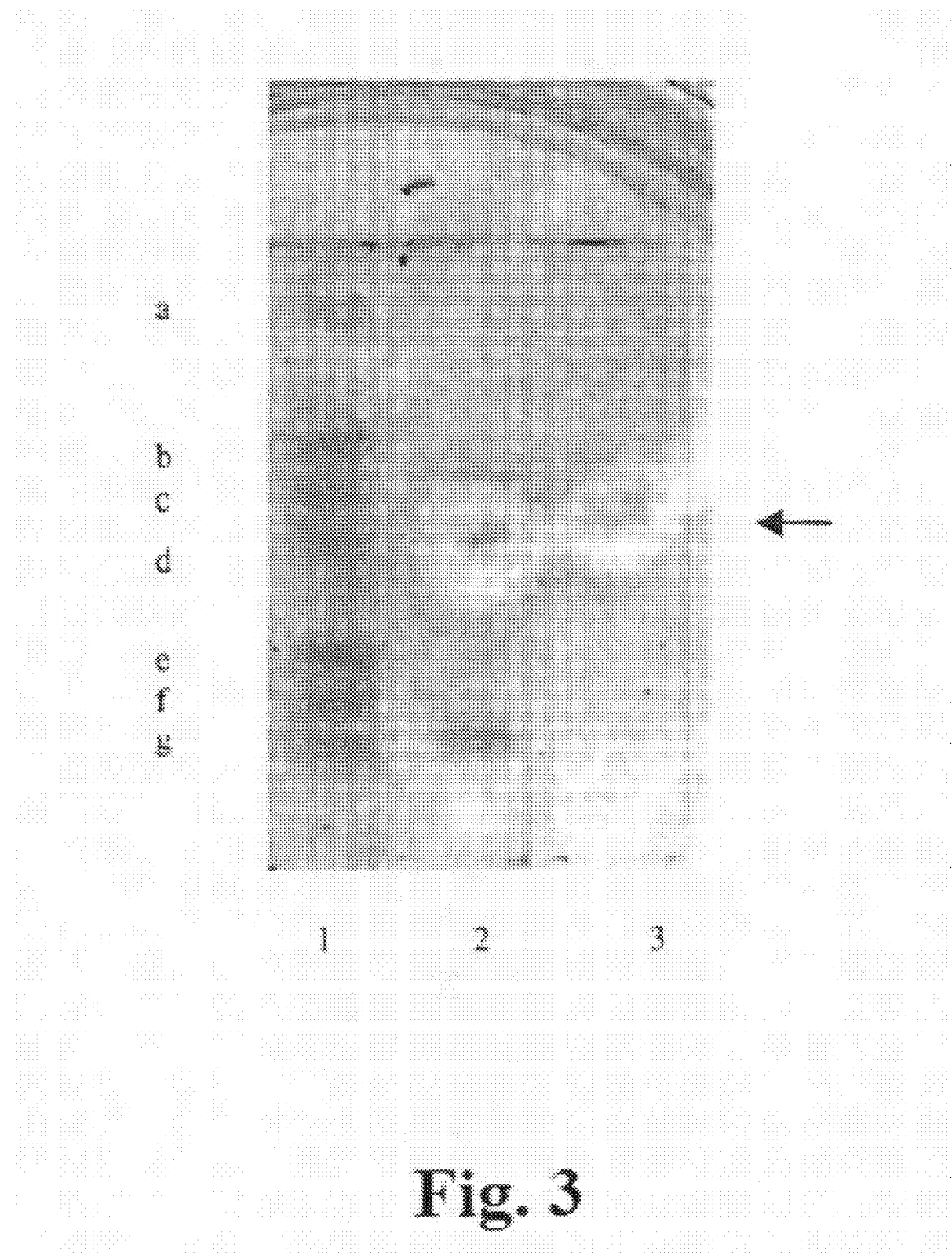
FIG. 3 is a photograph of a gel overlaid with *Campylobacter jejuni* to determine which band or bands corresponds to the antimicrobial activity and isoelectric point. This shows direct detection of bacteriocin 602 after isoelectrofocusing. Lane 1 shows pI standards (Protein Test Mixture 7, pI Marker Proteins, Serva): (a) 8.45, (b) 7.9, (c) 7.5, (d) 7.1, (e) 6.3, (f) 5.1, (g) 4.7. The band in Lane 2 (CAP 602) and the band in lane 3 (pure bacteriocin 602) correspond to the antimicrobial activity and the zone of growth inhibition.

Specimens of bacteriocins were placed on IEF gels (pH approximately 4.4-10.0) (Novex, San Diego, Calif.). The gels were run at about 100V for about 1 hour, 200V for about 2 hour, and 500V for about 30 minutes in XCM II™ Mini-Cell (Novex). Gels were washed with distilled water for about 4 hours without fixation followed by staining with Coomassie Blue G-250 to determine isoelectric points (pI) of the bacteriocins and their ability to inhibit the growth of the test strains as presented in FIGS. 2 and 3 and in Table 8.

TABLE 8

Antimicrobial activity of crude antimicrobial preparations (CAP) of bacteriocins evaluated by methods of a spot test, SDS-PAGE, and Isoelectrofocusing(IEF).

| Bacteriocin | Test strains | Inhibiting activity in Spot Test (AU/ml) | Inhibiting Activity measured by SDS-PAGE | Inhibiting Activity measured by IEF |
|---|---|---|---|---|
| 37 | *C. jejuni* ATCC 11168 | 12,800 | M.W. 3.5 kDa | band 1 pI = 4.8 |
|  | *S. enteritidis* 204 | 6,400 | M.W. 3.5 kDa | band 1 pI = 4.8 |
|  | *E. coli* O157:H7 904 | 12,800 | M.W. 3.5 kDa | band 1 pI = 4.8 |
| 602 | *C. jejuni* ATCC 11168 | 6,400 | M.W. 3.5 kDa | band 1 pI = 7.2 |
|  | *S. enteritidis* 204 | 3,200 | M.W. 3.5 kDa | band 1 pI = 7.2 |
|  | *E. coli* O157:H7 904 | 3,200 | M.W. 3.5 kDa | band 1 pI = 7.2 |
| 1580 | *C. jejuni* ATCC 11168 | 12,800 | M.W. 3.5 kDa | band 1 pI = 7.8 |
|  | *S. enteritidis* 204 | 6,400 | M.W. 3.5 kDa | band 1 pI = 7.8 |
|  | *E. coli* O157:H7 904 | 3,200 | M.W. 3.5 kDa | band 1 pI = 7.8 |

Example 5

Bacteriocins obtained as a crude antimicrobial preparation, as described above in Example 2, were purified by gel filtration and ion exchange chromatography. Crude antimicrobial preparation was injected into a Superose 12HR 16/50 column (Pharmacia, 1.6×50 cm) equilibrated with about 50 ml of phosphate-sodium buffer, pH approximately 5.9. Bacteriocins were eluted with the same buffer at a flow rate of about 0.85 ml/min. Activity of the eluted fractions were tested against three strains of *Campylobacter jejuni* L-4, B-1, and F-2. The concentration of the protein was measured by using the method described by Lowery et al., (Journal of Biological Chemistry, Volume 193, 1951). Analysis of fractions with higher antimicrobial activity was performed either on a Mono Q column (Pharmacia, 1.5×20 cm) or on a CM-Sepharose column (Pharmacia, 2.5×20 cm). The Mono Q HR 5/5 column was equilibrated with about 20 ml phosphate-sodium buffer (ph about 7.8) at a flow rate of about 5 ml/min. Bacteriocins were eluted with the same buffer in the presence of NaCl at concentrations of about 0.1%, 0.15%, 0.3%, and 0.5% at a flow rate of approximately 1.5 ml/min. The CM-Sepharose column was equilibrated with about 75 mM phosphate-sodium buffer (pH about 5.8) at a flow rate of about 5 ml/min. Bacteriocins were eluted with about 5 mM of buffer in the presence of NaCl at concentrations of from about 0.4% to about 1.2% at a flow rate of about 2 ml/min. Antimicrobial activity and protein concentrations for each fraction were determined.

Since fractions present in preparations 37, 114, 119, 592, and 602 varied in their molecular weights, Superose 12HR gel-filtration was the first step of purification (FIG. 1). Fractions generating peaks at approximately 280 nm were analyzed for their antagonistic activity against *C. jejuni* in a spot test (See Example 2 above), fractions of the first peak appeared to be most active. Since preparations 37, 114, 119, and 592 had an active fraction at pI=about 4.8, their purification was performed by Mono Q anion-exchange chromatography (FIG. 2) followed by elution of active fractions as a single peak at about 210 nm in the presence of about 0.3M NaCl. Cation-exchange chromatography was applied to purify CAP 602 because of the presence of an active peptide with a pI=about 7.2 (cationic protein). After, gel filtration of the fraction of the first peak, preparation 602 was further purified by CM cation-exchange chromatography. The active fraction was eluted as a single peak at about 280 nM in the presence of about 0.8 M NaCl. Purity was confirmed by MonoQ and C chromatographic methods. Results from purification of bacteriocin 37 are presented in Table 9. SDS-PAGE analysis showed that the purified peptides had molecular weight of approximately 3.5 kDa and application of isoelectrofocusing established a pI=about 4.8 for preparations 37, 114, 119, 592, and pI=about 7.2 for 602 (FIGS. 1 and 2).

The amino acid sequences of purified bacteriocins were determined by Edman degradation using a 491 cLC automatic sequencer (Applied Biosystems, USA). The bacteriocins were hydrolyzed in about 6M HCl under a vacuum at approximately 110° C. for about 72 hours. Primary sequences of bacteriocins 37, 602, and 1580 correspond to 30, 39, and 34 amino acid-containing peptides, respectively. Molecular weights of bacteriocins 37, 602, and 1580 were determined by mass spectrometry using a Voyager-DERP (Perkin-Elmer, USA). The MALDI-TOF system, a matrix-assisted laser desorption ionization time of flight system, was used along with matrix, 2-cyano-hydroxycinnamic acid. The amino acid sequences are:

```
602:
ATYYGNGLYCNKQKHYTWVDWNKASREIGKIIVNGWVQH    SEQ ID NO 2

1580:
VNYGNGVSCSKTKCSVNWGHTHQAFRVTSGVASG         SEQ ID NO 3

37:
FVYGNGVTSILVQAQFLVNGQRRFFYTPDK             SEQ ID NO 1
```

Calculated molecular weights of the peptides were about 3,520 kDa for bacteriocin 37, about 3,750 kDa for bacteriocin 602, and about 3,680 kDa for bacteriocin 1580. Analysis by MALDI-TOF revealed the following molecular weights: about 3,214 kDa for bacteriocin 37, about 3,864 kDa for bacteriocin 602, and about 3,486 kDa for bacteriocin 1580.

TABLE 9

Biochemical purification of bacteriocin 37

| Sample | Volume (ml) | Protein (mg/ml) | Specific Activity AU/mg protein | Purity % |
|---|---|---|---|---|
| Culture Supernatant | 150 | 1.5 | 17,066 | 0 |
| CAP (centrifugation (NH$_4$)$_2$SO$_4$) | 8.9 | 0.9 | 28,444 | 9.09 |
| Superose-12 Gel Filtration | 4 | 0.3 | 51,200 | 80.5 |
| Mono-Q anion-exchange chromatography | 1.8 | 0.19 | 134,736 | 98.8 |

Example 6

The influence of enzymes, temperature, and pH on bacteriocin activity was determined. About 10 ml of one of the following enzymes were transferred into tubes containing about 20 ml of bacteriocins: beta-chymotrypsin-about 100 mg/ml, proteinase K-about 200 mg/ml, papain-about 60 mg/ml, lysozyme-about 750 mg/ml, and lipase-about 100 mg/ml (all from Sigma-Aldrich Corp., St. Louis Mo.). After about a three hour incubation period at about 37° C., the mixture of bacteriocin and enzyme was analyzed for antimicrobial activity using the spot test as in Example 3. Untreated bacteriocins served as positive controls.

To study the thermostability of bacteriocins, about a 2 mg/ml sample was boiled in a water bath for about 15 minutes, cooled, and assessed in terms of their antimicrobial activity. Approximately 2 mg/ml of bacteriocin was used to evaluate the effect of pH. About 2 milliliters of sterile solutions, about 10 mM NaOH or about 10 mM HCl were added to samples to test pH from about 3 to about 10. Samples were incubated at about 37° C. for about 2 hours and 24 hours, and at about 90° C. for about 20 minutes. Samples were adjusted to pH about 7.2 by addition of about 4 mM sterile phosphate buffer and analyzed for their antimicrobial activity using the spot test as described above in Example 3.

The bacteriocins lost their antimicrobial activity after being treated with beta-chymotrypsin, proteinase K, and papain, but retained it when treated with lysozyme, lipase, or heating to about 90° C. (Table 10). They were stable at different values of pH ranging from about 3.0 to about 9.0, but became inactive at about pH 10 (Table 11).

TABLE 10

Effect of enzymes and temperature on antimicrobial activity of bacteriocins

| Treatment | Activity* |
|---|---|
| beta-chymotrypsin | − |
| proteinase K | − |
| Papain | − |
| lysozyme | + |
| lipase | + |
| 100° C., 15 minutes | + |

*activity determined by spot test, with *C. jejuni* ATCC 11168 as indicating strain.
+ presence of activity
− absence of activity after treatment with enzymes or exposure to temperature

TABLE 11

Effect of pH on activity of bacteriocin 37.

| | Activity determined by spot test with *C. jejuni* ATCC 11168 | | |
|---|---|---|---|
| pH | 20 min @ 90° C. | 2 h @ 37° C. | 24 h @ 37° C. |
| 3.0 | + | + | + |
| 5.0 | + | + | + |
| 6.2 | + | + | + |
| 7.0 | + | + | + |
| 8.4 | + | + | + |
| 9.1 | + | + | + |
| 10.0 | − | − | − |

+ presence of activity
− absence of activity

Example 7

Bacteriocin 602 was purified as described in Example 5. Purified bacteriocin 602 was added at a concentration of approximately 250 mg per kilogram of commercial poultry feed in polyvinylpyrrolidone as is known in the art. Bout 100 grams of a therapeutic composition made up with milled maize grain contains approximately 0.5 grams bacteriocin 602, approximately 1.25 grams of polyvinylpyrrolidone, and approximately 8.6% water. About 100 grams of this composition is added to about 2 kilograms of poultry feed. 1 day-, six day- and 18 day-old chicks were placed in groups in separate isolation units equipped with feeders, water, and filtered air supply. The food and water were supplied ad libitum. For 1 day-old chicks (Table 12), Group one chicks served as the control group which received free access to diet without added bacteriocin. These chicks were challenged at day one of life with strains L4 and B1 of *C. jejuni*, as described above in Example 1. The strains were administered by oral gavage at a concentration of approximately $2\times10^6$ in a volume of 0.2 ml. Five of the chicks were sacrificed at about 7 days after challenge and the remaining five were sacrificed at about 10 days after challenge. Group two chicks were challenged at day 1 of life with *C. jejuni* strains L4 and B1 as described above for Group one. The chicks were given free access to diet containing approximately 250 mg of bacteriocin 602 per kilogram of food for three days beginning from the $4^{th}$ day of life. Group two chicks were sacrificed about seven days after *C. jejuni* challenge. Group three chicks were challenged and fed as Group two chicks and sacrificed 10 days after challenge. Results are presented in Table 12.

TABLE 12

Therapeutic effects of bacteriocin 602 for experimentally induced *C. jejuni* infection in broilers.

| Group | Bird # | Time of Sacrifice after challenge in days | Concentration of *C. jejuni* gram/gram cecal content | Protection index in % |
|---|---|---|---|---|
| One | 1 | 7 | 6.63 | |
| | 2 | 7 | 6.18 | |
| | 3 | 7 | 6.15 | |
| | 4 | 7 | 5.87 | |
| | 5 | 7 | 6.21 | |
| | 6 | 10 | 9.00 | |
| | 7 | 10 | 8.68 | |
| | 8 | 10 | 8.95 | |
| | 9 | 10 | 9.34 | |
| | 10 | 10 | 8.99 | |
| Two | 1 | 7 | 0.00 | 100% |
| | 2 | 7 | 0.00 | 100% |
| | 3 | 7 | 6.60 | 0.94% |
| | 4 | 7 | 3.68 | 1.69% |
| | 5 | 7 | 3.15 | 1.97% |
| | 6 | 7 | 0 | 100% |
| | 7 | 7 | 0 | 100% |
| | 8 | 7 | 0 | 100% |
| | 9 | 7 | 0 | 100% |
| | 10 | 7 | 0 | 100% |
| Three | 1 | 10 | 0 | 100% |
| | 2 | 10 | 5.82 | 1.54% |
| | 3 | 10 | 0 | 100% |
| | 4 | 10 | 0 | 100% |
| | 5 | 10 | 3.41 | 2.64% |
| | 6 | 10 | 0 | 100% |
| | 7 | 10 | 0 | 100% |
| | 8 | 10 | 0 | 100% |
| | 9 | 10 | 0 | 100% |
| | 10 | 10 | 0 | 100% |

*Therapeutic diet prepared on the basis of commercial food intended for chicks aged 1-10 days.

For 6 day-old chicks, the control groups received free access to diet without added bacteriocin. These chicks were challenged on day 2 of the experiment with approximately $10^6$ CFU in about a 0.2 ml volume) of strains L-4, and B-1 of *C. jejuni*, as described in Example 1. The *C. jejuni* was administered by oral gavage. Chicks were sacrificed 4 days, 9 days, 11 days, and 14 days post challenge. Experimental chicks, having two groups, were given free access to diet with bacteriocin 602 encapsulated in polyvinylpyrrolidone beginning from day 6 of life. These chicks were challenged on day 2 of the experiment as above for the control chicks. Chicks were sacrificed at day 9 and 11 of life. Results are shown in Table 13 below.

TABLE 13

Treatment of experimental *C. jejuni*-associated infection in 6-day old chicks with bacteriocin 602 added to feed.

| Group | Chicks per group | Time of *C. jejuni* challenge and dose in CFU | Duration of feeding days | Age of sacrificed chicks | Concentration of *C. jejuni* per gram of cecal material |
|---|---|---|---|---|---|
| Control | 4 | $2^{nd}$ day $10^6$ CFU | — | 4 | $8 \times 10^8$ |
|  | 5 | $2^{nd}$ day $10^6$ CFU | — | 9 | $1.8 \times 10^8$ |
|  | 5 | $2^{nd}$ Day $10^6$ CFU | — | 11 | $1.02 \times 10^9$ |
|  | 5 | $2^{nd}$ Day $10^6$ CFU | — | 14 | $8.2 \times 10^8$ |
| Bacteriocin[8] 602 in Feed | 9 | $2^{nd}$ Day $10^6$ CFU | 3 | 9 | 4 CHICKS = 0<br>1 CHICK = $1 \times 10^1$<br>1 CHICK = $1 \times 10^2$<br>3 CHICKS = $1 \times 10^3$ |
|  | 8 | $2^{ND}$ Day $10^6$ CFU | 5 | 11 | 6 CHICKS = 0<br>1 CHICK0$1 \times 10^1$<br>1 CHICK = $1 \times 10^4$ |
|  | 9 | $2^{ND}$ Day $10^6$ CFU | 8 | 14 | 9 CHICKS = 0 |

[8]net dose administered to chicks for 3-day period = approximately 26.4 mg; 5-day = approximately 50.6 mg; 8-day = approximately 80.5 mg.

For 18-day old chicks, the control chicks received free access to diet without added bacteriocin. These chicks were challenged as above on day 15 of the experiment by oral gavage with a dose of $10^7$ CFU *C. jejuni* strains L-4 and B-1 in approximately a volume of 0.2 ml. Chicks were sacrificed at day 24 of the experiment. Chicks receiving conventional diet including bacteriocin 602 as described above were given free access to feed containing approximately 0.25 g bacteriocin 602 per kg of feed for about five days beginning on about the $19^{th}$ day of life. Net therapeutic dose is about 107.8 mg per chick. Chicks were sacrificed on about day 24 of life. Results are shown in Table 14 below.

TABLE 14

Treatment of experimental *C. jejuni*-associated infection in 18-day old chicks with bacteriocin 602 added to feed.

| Group | # of Chicks | Age and Dose of *C. jejuni* challenge CFU | Age of Sacrificed Chicks | Concentration (CFU) *C. jejuni* per gram of cecal material |
|---|---|---|---|---|
| Control | 5 | $15^{th}$ day $10^7$ CFU | 24 | $7.84 \times 10^9$ |
| Bacteriocin 602 Treatment | 10 | $15^{th}$ day $10^7$ CFU | 24 | 4 CHICKS = 0<br>4 CHICKS = $1.2 \times 10^2$<br>1 CHICK = $2 \times 10^7$<br>1 CHICK = $5.7 \times 10^8$ |

Chicks were challenged at 1-day of life and Control chicks were given free access to food and water without added bacteriocin. Chicks were challenged with approximately $10^6$ CFU of a mixture of strains L4 and B1 *C. jejuni* by oral gavage the $1^{st}$ day of life. Control chicks were sacrificed at day 17 of life. In experimental group I, 1-day old chicks were challenged as control chicks, given free access to feed with approximately 0.250 grams of bacteriocin 602 per kilogram of feed starting at day 14 of life and sacrificed at about day 17 of life; and group II chicks were challenged as control chicks at day 1 of life and were given free access to feed containing approximately 0.500 grams of bacteriocin 602 per kilogram of feed at day 14 of life; and sacrificed at day 17 of life, results are shown below in Table 15.

TABLE 15

Treatment of experimental *C. jejuni*-associated infection in chicks with bacteriocin 602 added to feed.

| Group | # of Chicks | Age and dose of *C. jejuni* Challenge in CFU | Concentration of *C. jejuni* per gram of cecal material at Day 17 of life |
|---|---|---|---|
| Control | 10 | 1-day old $10^6$ CFU | 2 CHICKS = $4.0 \times 10^6$<br>1 CHICK = $1.9 \times 10^7$<br>7 CHICKS = $0.3 \times 10^9$ |
| Treated with Feed containing 0.250 g/1 kilogram Feed | 16 | 1-day old $10^6$ CFU | 16 CHICKS = 0 |
| Treated with Feed containing 0.500/1 kilogram Feed | 16 | 1-day old $10^6$ CFU | 16 CHICKS = 0 |

The foregoing detailed description is for the purpose of illustration. Such detail is solely for that purpose and those skilled in the art can make variations without departing from the spirit and scope of the invention.

What is claimed is:

1. A therapeutic feed for animals comprising:

(a) an isolated bacteriocin produced by a *Paenibacillus polymyxa* strain NRRL B-30509 in amounts effective to at least reduce the levels of colonization of at least one target bacteria, (b) a therapeutic carrier, and (c) an animal feed.

2. The therapeutic feed of claim 1 wherein said bacteriocin has the amino acid sequence of SEQ ID NO 2.

3. A therapeutic animal feed comprising:

(a) an isolated bacteriocin having the amino acid sequence of SEQ ID NO 2, in amounts effective to at least reduce the levels of colonization by at least one target bacteria, (b) a therapeutic carrier, and (c) an animal feed.

4. A therapeutic feed for animals comprising:

(a) at least one isolated bacteriocin produced by a *Paenibacillus polymyxa* strain NRRL B-30509 in amounts effective to at least reduce the levels of colonization of at least one target bacteria, (b) a therapeutic carrier, and (c) an animal feed.

* * * * *

SEQUENCE LISTING

<160> NUMBER OF SEQ ID NOS: 21

<210> SEQ ID NO 1
<211> LENGTH: 30
<212> TYPE: PRT
<213> ORGANISM: Bacillus circulans

<400> SEQUENCE: 1

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30

<210> SEQ ID NO 2
<211> LENGTH: 39
<212> TYPE: PRT
<213> ORGANISM: Bacillus circulans

<400> SEQUENCE: 2

Ala Thr Tyr Tyr Gly Asn Gly Leu Tyr Cys Asn Lys Gln Lys His Tyr
1               5                   10                  15

Thr Trp Val Asp Trp Asn Lys Ala Ser Arg Glu Ile Gly Lys Ile Ile
            20                  25                  30

Val Asn Gly Trp Val Gln His
        35

<210> SEQ ID NO 3
<211> LENGTH: 34
<212> TYPE: PRT
<213> ORGANISM: Bacillus circulans

<400> SEQUENCE: 3

Val Asn Tyr Gly Asn Gly Val Ser Cys Ser Lys Thr Lys Cys Ser Val
1               5                   10                  15

Asn Trp Gly His Thr His Gln Ala Phe Arg Val Thr Ser Gly Val Ala
            20                  25                  30

Ser Gly

<210> SEQ ID NO 4
<211> LENGTH: 37
<212> TYPE: PRT
<213> ORGANISM: Lactococcus lactis

<400> SEQUENCE: 4

Thr Ser Tyr Gly Asn Gly Val His Cys Asn Lys Ser Lys Cys Trp Ile
1               5                   10                  15

Asp Val Ser Glu Leu Glu Thr Tyr Lys Ala Gly Thr Val Ser Asn Pro
            20                  25                  30

Lys Asp Ile Leu Trp
        35

<210> SEQ ID NO 5
<211> LENGTH: 37
<212> TYPE: PRT
<213> ORGANISM: Leuconostoc mesenteroides

<400> SEQUENCE: 5

Lys Tyr Tyr Gly Asn Gly Val His Cys Thr Lys Ser Gly Cys Ser Val
1               5                   10                  15

```
Asn Trp Gly Glu Ala Ala Ser Ala Gly Ile His Arg Leu Ala Asn Gly
            20                  25                  30

Gly Met Gly Phe Trp
        35

<210> SEQ ID NO 6
<211> LENGTH: 37
<212> TYPE: PRT
<213> ORGANISM: Leuconostoc gelidum

<400> SEQUENCE: 6

Lys Tyr Tyr Gly Asn Gly Val His Cys Thr Lys Ser Gly Cys Ser Val
1               5                   10                  15

Asn Trp Gly Glu Ala Phe Ser Ala Gly Val His Arg Leu Ala Asn Gly
            20                  25                  30

Gly Asn Gly Phe Trp
        35

<210> SEQ ID NO 7
<211> LENGTH: 36
<212> TYPE: PRT
<213> ORGANISM: Bifidobacterium bifidum

<400> SEQUENCE: 7

Lys Tyr Tyr Gly Asn Gly Val Thr Cys Gly Leu His Asp Cys Arg Val
1               5                   10                  15

Asp Arg Gly Lys Ala Thr Cys Gly Ile Ile Asn Asn Gly Gly Met Trp
            20                  25                  30

Gly Asp Ile Gly
        35

<210> SEQ ID NO 8
<211> LENGTH: 43
<212> TYPE: PRT
<213> ORGANISM: Lactobacillus sake

<400> SEQUENCE: 8

Lys Tyr Tyr Gly Asn Gly Val His Cys Gly Lys His Ser Cys Thr Val
1               5                   10                  15

Asp Trp Gly Thr Ala Ile Gly Asn Ile Gly Asn Asn Ala Ala Ala Asn
            20                  25                  30

Trp Ala Thr Gly Gly Asn Ala Gly Trp Asn Lys
        35                  40

<210> SEQ ID NO 9
<211> LENGTH: 43
<212> TYPE: PRT
<213> ORGANISM: Enterococcus mundtii

<400> SEQUENCE: 9

Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ser Ala Ala Asn
            20                  25                  30

Leu Ala Thr Gly Gly Ala Ala Gly Trp Ser Lys
        35                  40

<210> SEQ ID NO 10
<211> LENGTH: 41
<212> TYPE: PRT
<213> ORGANISM: Lactobacillus sake
```

```
<400> SEQUENCE: 10

Ala Arg Ser Tyr Gly Met Gly Val Tyr Cys Asn Met Lys Lys Cys Trp
1               5                   10                  15

Val Asn Arg Gly Glu Ala Thr Gln Ser Ile Ile Gly Gly Met Ile Ser
            20                  25                  30

Gly Trp Ala Ser Gly Leu Ala Gly Met
        35                  40

<210> SEQ ID NO 11
<211> LENGTH: 44
<212> TYPE: PRT
<213> ORGANISM: Carnobacterium piscicola

<400> SEQUENCE: 11

Lys Tyr Tyr Gly Asn Gly Val Ser Cys Asn Lys Asn Gly Cys Thr Val
1               5                   10                  15

Asp His Ser Lys Ala Ile Gly Ile Ile Gly Asn Asn Ala Ala Ala Asn
            20                  25                  30

Leu Thr Thr Gly Gly Ala Ala Gly Trp Asn Lys Gly
        35                  40

<210> SEQ ID NO 12
<211> LENGTH: 43
<212> TYPE: PRT
<213> ORGANISM: Carnobacterium piscicola

<400> SEQUENCE: 12

Ala Ile Ser Tyr Gly Asn Gly Val Tyr Cys Asn Lys Glu Lys Cys His
1               5                   10                  15

Val Asn Lys Ala Glu Asn Lys Gln Ala Ile Thr Gly Ile Val Ile Gly
            20                  25                  30

Gly Trp Ala Ser Ser Leu Ala Gly Met Gly His
        35                  40

<210> SEQ ID NO 13
<211> LENGTH: 48
<212> TYPE: PRT
<213> ORGANISM: Carnobacterium piscicola

<400> SEQUENCE: 13

Val Met Tyr Gly Asn Gly Val Ser Cys Ser Lys Thr Lys Cys Ser Val
1               5                   10                  15

Asn Trp Gly Gln Ala Phe Gln Glu Arg Tyr Thr Ala Gly Ile Asn Ser
            20                  25                  30

Phe Val Ser Gly Val Ala Ser Gly Ala Gly Ser Ile Gly Arg Arg Pro
        35                  40                  45

<210> SEQ ID NO 14
<211> LENGTH: 40
<212> TYPE: PRT
<213> ORGANISM: Lactobacillus sake
<220> FEATURE:
<221> NAME/KEY: misc_feature
<222> LOCATION: (30)..(30)
<223> OTHER INFORMATION: Xaa can be any naturally occurring amino acid

<400> SEQUENCE: 14

Thr Lys Tyr Tyr Gly Asn Gly Val Tyr Cys Asn Ser Lys Lys Cys Trp
1               5                   10                  15

Val Asp Trp Gly Gln Ala Ala Gly Gly Ile Gln Thr Trp Xaa Gly Trp
```

```
                20              25                  30
Leu Gly Gly Ala Ile Pro Gly Lys
        35                  40

<210> SEQ ID NO 15
<211> LENGTH: 43
<212> TYPE: PRT
<213> ORGANISM: Bacillus circulans

<400> SEQUENCE: 15

Ala Thr Tyr Tyr Gly Asn Gly Leu Tyr Cys Asn Lys Gln Lys Cys Trp
1               5                   10                  15

Val Asp Trp Asn Lys Ala Ser Arg Glu Ile Gly Lys Ile Ile Val Asn
            20                  25                  30

Gly Trp Val Gln His Gly Pro Trp Ala Pro Arg
        35                  40

<210> SEQ ID NO 16
<211> LENGTH: 44
<212> TYPE: PRT
<213> ORGANISM: Enterococcus faecium

<400> SEQUENCE: 16

Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
        35                  40

<210> SEQ ID NO 17
<211> LENGTH: 47
<212> TYPE: PRT
<213> ORGANISM: Enterococcus faecium

<400> SEQUENCE: 17

Thr Thr His Ser Gly Lys Tyr Tyr Gly Asn Gly Val Tyr Cys Thr Lys
1               5                   10                  15

Asn Lys Cys Thr Val Asp Trp Ala Lys Ala Thr Thr Cys Ile Ala Gly
            20                  25                  30

Met Ser Ile Gly Gly Phe Leu Gly Gly Ala Ile Pro Gly Lys Cys
        35                  40                  45

<210> SEQ ID NO 18
<211> LENGTH: 44
<212> TYPE: PRT
<213> ORGANISM: Pediococcus acidilactici

<400> SEQUENCE: 18

Lys Tyr Tyr Gly Asn Gly Val Thr Cys Gly Lys His Ser Cys Ser Val
1               5                   10                  15

Asp His Gly Lys Ala Thr Thr Cys Ile Ile Asn Met Gly Ala Gly Ala
            20                  25                  30

Trp Ala Thr Gly Gly His Gln Gly Asn His Lys Cys
        35                  40

<210> SEQ ID NO 19
<211> LENGTH: 43
<212> TYPE: PRT
<213> ORGANISM: Carnobacterium divergens
```

-continued

```
<400> SEQUENCE: 19

Thr Lys Tyr Tyr Gly Asn Gly Val Tyr Cys Asn Ser Lys Lys Cys His
1               5                   10                  15

Val Asp Trp Gly Gln Ala Ser Gly Cys Ile Gly Gln Thr Val Val Gly
            20                  25                  30

Gly Trp Leu Gly Gly Ala Arg Pro Gly Lys Cys
        35                  40

<210> SEQ ID NO 20
<211> LENGTH: 44
<212> TYPE: PRT
<213> ORGANISM: Bacillus coagulans

<400> SEQUENCE: 20

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Thr His Lys Cys
        35                  40

<210> SEQ ID NO 21
<211> LENGTH: 10
<212> TYPE: PRT
<213> ORGANISM: Artificial Sequence
<220> FEATURE:
<223> OTHER INFORMATION: consensus sequence

<400> SEQUENCE: 21

Tyr Gly Asn Gly Val Cys Cys Val Trp Ala
1               5                   10
```